(12) United States Patent
Eberting

(10) Patent No.: US 12,233,034 B2
(45) Date of Patent: *Feb. 25, 2025

(54) FORMULATIONS FOR EPIDERMAL REPAIR

(71) Applicant: Claridei Laboratories, Inc., Alpine, UT (US)

(72) Inventor: Cheryl Lee Eberting, Alpine, UT (US)

(73) Assignee: Claridei Laboratories, Inc., Alpine, UT (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/493,801

(22) Filed: Oct. 4, 2021

(65) Prior Publication Data

US 2022/0031640 A1 Feb. 3, 2022

Related U.S. Application Data

(63) Continuation of application No. 16/008,786, filed on Jun. 14, 2018, now Pat. No. 11,135,184, which is a continuation of application No. 14/907,479, filed as application No. PCT/US2014/048226 on Jul. 25, 2014, now abandoned.

(60) Provisional application No. 62/005,702, filed on May 30, 2014, provisional application No. 61/968,078, filed on Mar. 20, 2014, provisional application No. 61/896,215, filed on Oct. 28, 2013, provisional application No. 61/858,513, filed on Jul. 25, 2013.

(51) Int. Cl.
| | |
|---|---|
| *A61K 8/365* | (2006.01) |
| *A61K 8/36* | (2006.01) |
| *A61K 8/37* | (2006.01) |
| *A61K 8/41* | (2006.01) |
| *A61K 8/42* | (2006.01) |
| *A61K 8/44* | (2006.01) |
| *A61K 8/49* | (2006.01) |
| *A61K 8/55* | (2006.01) |
| *A61K 8/63* | (2006.01) |
| *A61K 8/68* | (2006.01) |
| *A61K 9/00* | (2006.01) |
| *A61K 31/133* | (2006.01) |
| *A61K 31/164* | (2006.01) |
| *A61K 31/19* | (2006.01) |
| *A61K 31/20* | (2006.01) |
| *A61K 31/23* | (2006.01) |
| *A61K 31/455* | (2006.01) |
| *A61K 31/573* | (2006.01) |
| *A61K 31/575* | (2006.01) |
| *A61K 47/12* | (2006.01) |
| *A61K 47/14* | (2017.01) |
| *A61K 47/18* | (2017.01) |
| *A61K 47/24* | (2006.01) |
| *A61K 47/28* | (2006.01) |
| *A61Q 19/00* | (2006.01) |

(52) U.S. Cl.
CPC ............ *A61K 31/164* (2013.01); *A61K 8/361* (2013.01); *A61K 8/365* (2013.01); *A61K 8/37* (2013.01); *A61K 8/41* (2013.01); *A61K 8/42* (2013.01); *A61K 8/44* (2013.01); *A61K 8/4926* (2013.01); *A61K 8/55* (2013.01); *A61K 8/63* (2013.01); *A61K 8/68* (2013.01); *A61K 9/0014* (2013.01); *A61K 31/133* (2013.01); *A61K 31/19* (2013.01); *A61K 31/20* (2013.01); *A61K 31/23* (2013.01); *A61K 31/455* (2013.01); *A61K 31/573* (2013.01); *A61K 31/575* (2013.01); *A61K 47/12* (2013.01); *A61K 47/14* (2013.01); *A61K 47/18* (2013.01); *A61K 47/24* (2013.01); *A61K 47/28* (2013.01); *A61Q 19/00* (2013.01); *A61Q 19/007* (2013.01); *A61K 2800/48* (2013.01); *A61K 2800/5922* (2013.01)

(58) Field of Classification Search
CPC .......... A61K 31/164; A61K 8/41; A61K 8/37; A61K 8/365; A61K 8/361; A61K 8/498; A61K 8/63; A61K 8/675; A61K 8/68
See application file for complete search history.

(56) References Cited

U.S. PATENT DOCUMENTS

| | | | |
|---|---|---|---|
| 3,855,140 | A | 12/1974 | Billany |
| 5,520,918 | A | 5/1996 | Smith |
| 5,643,889 | A | 7/1997 | Elias |
| 5,833,998 | A | 11/1998 | Biedermann |
| 2003/0026820 | A1 | 2/2003 | De Lacharriere et al. |
| 2003/0091605 | A1 | 5/2003 | Mummert et al. |
| 2003/0198610 | A1 | 10/2003 | Nakayama |

(Continued)

FOREIGN PATENT DOCUMENTS

| | | |
|---|---|---|
| CN | 1513557 A | 7/2004 |
| EP | 2692334 A1 | 2/2014 |

(Continued)

OTHER PUBLICATIONS

European Patent Application 14297310, Extended European Search Report dated Nov. 8, 2016, 8 pp.

(Continued)

*Primary Examiner* — Amanda L. Aguirre
*Assistant Examiner* — Chris E Simmons
(74) *Attorney, Agent, or Firm* — PCFB, LLC; Justin K. Flanagan

(57) ABSTRACT

The present disclosure is directed to dermatological formulations and their use for treating a variety of dermatological diseases and disorders, and for repairing and restoring a disrupted epidermal barrier, inhibiting inflammation, restoring a proper environment for maintaining a balanced symbiotic microbiome, and inhibiting the growth of pathogenic microorganisms in the epidermis—the outer layer of mammalian skin.

20 Claims, 2 Drawing Sheets

(56) References Cited

U.S. PATENT DOCUMENTS

| | | |
|---|---|---|
| 2004/0105894 A1 | 6/2004 | Gupta |
| 2004/0120917 A1 | 6/2004 | Perrier et al. |
| 2007/0141000 A1 | 6/2007 | Nishumura et al. |
| 2008/0104570 A1 | 9/2008 | Montanari |
| 2009/0017147 A1 | 1/2009 | Lintner et al. |
| 2010/0249060 A1 | 9/2010 | Smith |
| 2010/0291007 A1 | 11/2010 | Mahe et al. |
| 2014/0018443 A1 | 1/2014 | Yamamoto |

FOREIGN PATENT DOCUMENTS

| | | |
|---|---|---|
| JP | 58140007 | 8/1983 |
| JP | 10316555 A | 12/1998 |
| JP | H11-292765 A | 10/1999 |
| JP | 2009155265 A | 7/2009 |
| JP | 2009167134 A | 7/2009 |
| JP | 2009184951 A | 8/2009 |
| JP | 2013053073 A | 3/2013 |
| WO | 1994000127 A1 | 1/1994 |
| WO | 2008104570 A2 | 9/2008 |
| WO | 2010039490 A3 | 4/2010 |
| WO | 20120133817 A | 10/2012 |
| WO | 2015013634 A1 | 1/2015 |

OTHER PUBLICATIONS

International Application No. PCT/US2014/048226, International Search Report (ISR) and Written Opinion (WO) dated Oct. 27, 2014, 16 pp.

"An Ester Product-Tainolin" ISIS/isoste-ryl, http://www.tnjc.com.tw/producUctfapisostea ryl+isostearate/518, 1 p.

Argarwal, et al., Inhibition of mouse skin tumor-initiating activity of DMBA by chronic oral feeding of glycymhizin in drinking water, Nutri Cancer. 1991; 15(3-4) : 187-93.

Bernstein, et al., The Polyhydroxy Acid Gluconolactone Protects Against Ultraviolet Radiation in an In Vitro Model of Cutaneous Photoaging, Dermatol Surg. Feb. 2004; 30 (2pt1) 189-95; discussion 196.

Cherng, et al., "Molecular Mechanisms Underlying Chemopreventative Activities of Glycymhizic Acid against UVB-Radiation-Induced Carinogenisis in SKH-1 Hairless Mouse Epidermis," Radiation Research Society, 2011, p. 177-186.

Long, et al., 188-Glycynthetinic Acid Inhibits MRSA Survival and Attenuates Virulence Gene Expression, Antimicrob Agents Chemother. Oct. 31, 2012, p. 241 -247.

Macheleidt, et al., Deficiency of epidermal protein-bound omega-hydroxyceramides in atopic dermatitis, J Invest Dermatol. Jul. 2002; 119(1) : 166-73.

Pennick, et al., The effect of an amphiphilic self-assembled lipid lamellar phase on the relief of dry slkin, Int J Cosmet Sci. Dec. 2012; 34(6): 567-74. Doi: 1111/j.1468-2494.2012.00749.x. ePulb Sep. 1, 2012, 9 pp.

Rossi, et al., Effects of Glycymhizin on UVB-irradiated Melanoma Cells, In Vivo. Jan.-Feb. 2005, 19(1): 319-22.

Saeedi, et al., The treatment of atopic dermatitis with licorice gel, Journal of Dermatological Treatment, vol. 14, No. 3, Sep. 2003, pp. 153-157.

Teelucksingh, et al., Potentation of Hydrocotisone Activity in Skin by Glycyrrhetinic Acid, The Lancet, May 5, 1990, 335 (8697): 1060-1063.

Wu, et al., Topical Application of Nicotinamide in the Treatment of Some Skin Diseases, Int. J. Dermatol. Venereol, May 2006, vol. 32, No. 3.

PCT International Patent Application No. PCT/US2014/048226, International Search Report Mailed Oct. 27, 2014, 3 pp.

U.S. Appl. No. 14/907,479, Non-Final Office Action mailed Dec. 14, 2017, 11 pp. (see p. 7).

Janssen Cosmetics. Encyclopedia of Ingredients: Isostearyl stearate. Copyright: Janssen Cosmetics GmbH D-52005 Aachen (Germany) www.janssen-cosmetics.com, Dec. 4, 2011.

U.S. Appl. No. 16/008,786, Non-Final Office Action mailed Mar. 6, 2020, 15 pp.

U.S. Appl. No. 16/008,786, Final Office Action mailed Sep. 23, 2020, 21 pp.

FORMULATIONS FOR EPIDERMAL REPAIR

RELATED APPLICATIONS

This application is a continuation of U.S. patent application Ser. No. 16/008,786 filed Jun. 14, 2018, titled "Formulations for Epidural Repair" and issuing on Oct. 5, 2021 as U.S. Pat. No. 11,135,184, which is a continuation of U.S. patent application Ser. No. 14/907,479 filed Jan. 25, 2016, which is the U.S. National Stage of International Application No. PCT/US2014/048226 filed Jul. 25, 2014, which claims priority to U.S. Provisional Application No. 61/858,513 filed Jul. 25, 2013, U.S. Provisional Application No. 61/896,215 filed Oct. 28, 2013, U.S. Provisional Application No. 61/968,078 filed Mar. 20, 2014, and U.S. Provisional Application No. 62/005,702 filed May 30, 2014. The contents of each of the applications noted above are hereby incorporated by reference in their entireties.

TECHNICAL FIELD

The present disclosure is directed to dermatological formulations and their use for repairing and restoring a disrupted epidermal barrier. The disclosed formulations are designed to supplement and replenish the natural lipid components of the epidermis, inhibit inflammation, restore the conditions required for maintaining a balanced symbiotic epidermal microbiome, and inhibit the growth of pathogenic microorganisms in the epidermis the outer layer of mammalian skin. The disclosed formulations are useful for the treatment of subjects suffering from skin or mucous membrane disturbances characterized by epidermal disruption, inflammation, and, in some embodiments, superinfection with pathogenic microorganisms.

BACKGROUND

Human skin is composed of several morphologically distinct layers. The outer-most layer of the skin, the epidermis, is composed of 4 to 5 sub-layers depending on where on the body the skin is located. These sub-layers, from the outer-most layer to the inner-most layer, include the stratum corneum, the stratum lucidum (which is present only in thick skin, such as the soles of feet and palms of hands), the stratum granulosum, the stratum spinosum and the stratum basale.

The underlying layers of the epidermis are referred to as the "viable epidermis," and form a dynamic, constantly self-renewing tissue that ultimately generates the stratum corneum—the layer exposed to the external environment. Skin cells, known as keratinocytes, grow and divide within the basal layer, and undergo a number of changes in both structure and composition as they migrate outwards through the stratum spinosum and stratum granulosum to the stratum corneum, ultimately differentiating into corneocytes, which make up the stratum corneum.

Corneocytes of the stratum corneum are flat, dead cells comprised mostly of keratin filaments and water, and surrounded by a densely cross-linked protein layer (the "cornified envelope") that is, in turn, chemically linked to a lipid envelope. The lipid envelope acts as an interface between the stacked layers of corneocytes, forming a lipophilic and non-polar layer between the hydrophilic corneocytes. The intercellular lipid layers between layers of corneocytes are a complex matrix consisting of a wide variety of ceramides, cholesterol, cholesterol esters, and free fatty acids. Although estimates vary, one study using advanced and carefully controlled methods revealed these lipid layers comprise, on average, about 47% ceramides; 24% cholesterol; 18% cholesterol esters; and 11% fatty acids, by weight. (Norlén, et al., Inter- and intra-individual differences in human stratum corneum lipid content related to physical parameters of skin barrier function in vivo. *J. Invest. Dermatol.* 1999 January; 112(1):72-7.) The vast majority of these lipids arise from the secretory organelles, known as lamellar bodies, or lamellar granules, within keratinocytes. These lamellar granules fuse with the cell membrane and release their contents into the extracellular space once the keratinocytes reach the stratum granulosum stratum corneum interface. Following their release, these lipids self-organize into the lamellar sheets that are a distinctive molecular characteristic of the stratum corneum.

The stratum corneum of the epidermis is primarily responsible for the water permeability barrier function of the skin, which is critical for preventing excessive dryness of the skin, as well as dehydration of the underlying tissues. Three main factors contribute to the establishment of this water permeability barrier within the stratum corneum: First, the intercellular, hydrophobic lipids form the only continuous pathways through the stratum corneum, and thereby block the transport of water molecules. Second, the corneocytes, which are surrounded by hydrophobic envelopes, are tightly linked to each other by specialized connective organelles known as corneodesmosomes. Third, the intracellular and extracellular hygroscopic materials known as natural moisturizing factors specifically retain water in the outer layer of the stratum corneum.

Moreover, the intercellular lipids in the stratum corneum of human skin form two lamellar phases (extended lamellar sheets of ordered lipid molecules) in two planes that fie parallel to the skin surface, with repeat distances of approximately 6 and 13 nm. These lamellar phases are respectively referred to as the short periodicity phase and the long periodicity phase. Within these lamellar phases the lipids are highly organized in a tightly-packed, mostly lateral, orthorhombic state. The orthorhombic packing, in addition to the presence of the long periodicity phase, is thought to be critical for normal barrier function.

It is believed that the long alkyl chains of the fatty acids and lipids within the lipid matrix of the stratum corneum are needed to induce the formation of the orthorhombic lattice observed in mixtures of ceramides and cholesterols. Furthermore, it has been shown, using tape stripping and electron microscopy that this highly organized lipid lamellar phase is missing from between the corneocytes in the outer most layers of dry skin.

From the above, it is clear that the human epidermis comprises a complex and heterogeneous mix of lipids, predominantly consisting of saturated lipids, cholesterol, and cholesterol esters, and long-chained fatty acids, with the saturated lipids being primarily a complex mixture of different types of ceramides. This heterogeneous mix of lipids is largely responsible for the "epidermal barrier" formed by healthy human skin.

A healthy, intact epidermal barrier plays a vital role in protecting mammals, and particularly humans, from the outside world. It serves as a physical barrier to simultaneously prevent the entry of harmful pathogens, irritants, allergens and other noxious chemical species, and the exit of excessive amounts of water, thereby providing protection from infection, irritation and dehydration. Moreover, healthy human skin, with its intact epidermal barrier, plays an important role in thermoregulation, and provides a relatively strong exterior layer that is resistant to physical damage by abrasion or puncture.

In contrast, a disrupted and dysfunctional epidermal barrier is a hallmark of atopic dermatitis, xerosis, ichthyosis, irritant dermatitis, allergic contact dermatitis, dyshidrosis, seborrheic dermatitis, psoriasis, all forms of cutaneous lupus erythematosus (CLE) including acute, subacute, and chronic cutaneous lupus, rosacea, acne, and many other papulosquamous skin disorders. Similarly, it appears that a disrupted and dysfunctional epidermal barrier is a hallmark of many, if not all, forms of photodermatoses, including idiopathic, genetic, metabolic and exogenous photodermatoses. It is widely believed that such a dysfunctional barrier can result from a perturbation—deficiency, surplus or alteration—of the lipid species that are normally present in an intact, healthy epidermis. Additionally, abnormalities in the desquamation of the epidermis, an overly exuberant inflammatory process, or the loss or imbalance of the naturally occurring antibacterial lipids within the epidermis, have been implicated in a subset of these diseases. Consequently, there is a need for therapeutic compositions that can be administered to repair a disrupted epidermal barrier and restore an intact healthy epidermal barrier. Moreover, there is a need for methods of treatment that utilize such therapeutic compositions.

The formulations disclosed herein address multiple defects in the epidermal barrier that are known from studies of dermatological diseases and Disorders, and do so in a targeted and synergistic fashion. The disclosed formulations provide a combination of essential skin lipid species that are often found to be deficient in disrupted skin, to restore an intact, healthy epidermal barrier. These formulations specifically exclude those skin lipid species that are found to be in excess in diseased skin. In addition to providing essential lipid species, the disclosed formulations also provide specific anti-inflammatory and antimicrobial components, and components to, establish an appropriately acidic pH of the skin, so that the skin supports the presence of synergistic beneficial microbiota and resists invasion and superinfection by harmful or pathogenic microorganisms. The formulations also provide components designed to establish and maintain an appropriate calcium gradient within the skin so as to induce the viable epidermis to synthesize and secrete the lipids, and particularly ceramides, that comprise the lamellar phases crucial in establishing an intact, effective epidermal barrier.

DETAILED DESCRIPTION

Figure 1:
FIG. 1 depicts the chest and neck area of a patient having cutaneous lupus erythematosus, prior to treatment with the disclosed formulations.

It has been discovered that topical application of formulations comprising combinations of sphingolipids (e.g., phytosphingolipids, such as ceramide 3), cholesterol esters, very long chained fatty acids, and, optionally, fatty alcohol, esters of fatty acids such as isostearyl isostearate, can be used to treat epidermal barrier defects and/or repair, replenish or maintain an effective epidermal barrier. It has also been discovered that glycyrrhetinic acid, and particularly 18β-glycyrrhetinic acid, which has anti-inflammatory, antiviral, antifungal, antiprotozoal, and antibacterial activities, when applied topically along with a glucocorticoid and/or niacinamide, either in a simple combination, or in combination with the formulations of sphingolipids, cholesterol esters, very long chained fatty acids, and, optionally, fatty alcohol esters of fatty acids disclosed herein, can potentiate the anti-inflammatory activity of the glucocorticoid and can therefore be used to treat epidermal barrier defects and/or repair, replenish or maintain an effective epidermal barrier. It has further been discovered that gluconolactone can be used in combination with the formulations of sphingolipids, cholesterol esters, very long chained fatty acids, and optionally fatty alcohol esters of fatty acids disclosed herein, in the presence or absence of 18β-glycyrrhetinic acid and/or a glucocorticoid and/or niacinamide, to establish and maintain an acidic pH within the epidermis that is important for treating epidermal barrier defects and/or repairing, replenishing or maintaining an effective epidermal barrier. It has further been discovered that the effectiveness of the formulations disclosed herein can be enhanced by reestablishing a gradient of calcium ions ($Ca^{2+}$) within diseased epidermis that is reminiscent of the calcium ion gradient observed in healthy epidermal tissues. The components of the formulations disclosed herein have been chosen to work synergistically, by addressing characteristic defects observed in defective or diseased epidermal tissue as identified in human patients suffering from specific dermatological diseases or disorders. As described in more detail in the disclosure and examples provided below, other ingredients are envisioned as components of these formulations, and different combinations of the disclosed ingredients may show greater efficacy in treating specific dermatological diseases and disorders by addressing the defects that are characteristically found in these diseases and disorders.

While not wishing to be bound by any one theory, the components of the compositions and formulations disclosed herein work synergistically to repair and restore the epidermal barrier by supplementing the natural lipid components of the skin, while also correcting other imbalances, such as alterations in pH, calcium gradient, and associated alterations in microbial flora, commonly observed in diseased skin, and while reducing inflammation resulting from a variety of causes.

Definitions

As used herein, the term "epidermal barrier" or "barrier" refers to those characteristics or properties of healthy skin that isolate and protect underlying living tissue from the external environment. Such characteristics or properties of the epidermal barrier serve to protect the body from infection by pathogens, inflammation in response to irritants or allergens, and excessive transepidermal water loss, etc.

The term "therapeutically effective amount," as used herein, refers to any amount of a specific component or combination of components (i.e., formulation), that will cause a reduction of symptoms, or relief from symptoms, when applied, either once, or repeatedly over time. Therapeutically effective amounts can be readily determined by skilled artisans using routine experimentation using tests and measures commonly employed in the art, or can be based upon the subjective response of patients undergoing treatment. In those formulations where the components work synergistically to restore the epidermal barrier, the therapeutically effective amounts of each component, when used in combination, may be found to be less than the therapeutically effective amounts when the components are used separately.

As used herein, "microbiome" refers to the totality of microbiota (i.e., microorganisms), their genetic elements (genomes, etc.), and environmental interactions in a particular environment. Importantly, the skin can be considered as an ecosystem supporting a range of symbiotic microbial communities that live in distinct niches. Studies characterizing the microbiota that inhabit these different niches, and their symbiotic interactions with the innate immune defense system of the skin, are beginning to provide insights into the effects this microbiota has on the balance between skin health and disease (Gallo and Nakatsuji, Microbial symbiosis with the innate immune defense system of the skin. *J. Invest. Dermatol.* 2011 October; 131(10): 1974.80). The effectiveness of antimicrobial agents in the management of some common skin disorders supports a role for microbes in pathophysiology. Elucidation of the baseline skin microbiomes is the first step toward testing the therapeutic potential of manipulating the microbiome in skin disorders. Grice, et al., Topographical and temporal diversity of the human skin microbiome. *Science* 2009 May 29; 324(5931): 1190-2. Indeed, an initial study of psoriasis (Gao, et al., Substantial alterations of the cutaneous bacterial biota in psoriatic lesions. *PLoS ONE,* 2008; 3(7); e2719) and an animal model of ichthyosis (Scharschmidt, et al., Filaggrin deficiency confers a paracellular barrier abnormality that reduces inflammatory thresholds to irritants and haptans. *J Invest Dermatol.* 2009 September; 124(3): 496-506) revealed selective microbial shifts associated with skin diseases. Hence, targeted therapies to maintain, healthy skin might require not only inhibiting the growth of pathogenic bacteria, but also promoting the growth of symbiotic bacteria. Grice, et al., Topographical and temporal diversity of the human skin microbiome. *Science* 2009 May 29: 324(5931): 1190-2.

While not wishing to be bound by any one theory, it is believed that measures taken to restore a balanced symbiotic skin microbiome can treat specific forms of dermatitis and other dermatological conditions. Hence, one of the objectives behind the formulations of the present disclosure is to correct abnormal aspects of diseased epidermis to promote the establishment and maintenance of a balanced symbiotic skin microbiome. It is believed that this can be accomplished by using the disclosed formulations to address imbalances in such factors as the lipid composition, and particularly the composition of lipids known to suppress growth of pathogenic microorganism, epidermal pH, and epidermal calcium gradient. Additionally, the use of components with known antibiotic activities to specifically impact the skin microbiome is contemplated.

Components of the Disclosed Formulations:

Epidermal sphingolipids are a class of lipids comprising, for example, ceramides, acylceramides, glycoceramides or glucosylceramides, and sphingomyelin. All of these compounds contain a sphingosine, or closely-related "sphingoid base" (i.e., dihydrosphingosine, phytosphingosine, or 6-hydroxy sphingosine) bound to either an acyl (non-hydroxy) fatty acid, an α-hydroxy fatty acid, or an esterified ω-hydroxy fatty acid, through an amide linkage at the amino group of the sphingosine. In some cases, these sphingolipids contain a saccharide moiety (i.e., monosaccharide or an oligosaccharide) linked by a glycosidic bond to the terminal hydroxyl group of the sphingosine moiety. Such compounds are known as "glucosylceramides."

Generically, sphingolipids can be described as compounds of Formula I:

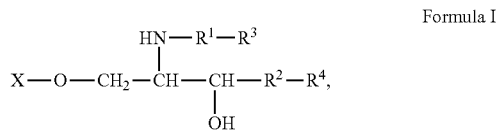

Formula I wherein,
X is either H—, a monosaccharide, or an oligosaccharide;
$R^1$ is either —(C=O)— or —$CH_2$—;
$R^2$ is either or —(CH=CH)— or —(CHOH)—$CH_2$—;
$R^3$ is any one of the following:
 (a) $C_{10}$-$C_{36}$ alkyl
 (b) α-hydroxy-$C_{10}$-$C_{36}$ alkyl;
 (c) ω-hydroxy-$C_{10}$-$C_{36}$ alkyl;
 (d) α,ω-hydroxy-$C_{10}$-$C_{36}$ alkyl; or
 (e) alkanoyl as define by Formula II:

$$R^5\text{—O—}\overset{\overset{\displaystyle O}{\|}}{C}\text{—}R^6,$$

Formula II wherein
$R^5$ is either divalent $C_{10}$-$C_{36}$, alkyl or divalent α-hydroxy-$C_{10}$-$C_{36}$ alkyl, and
$R^6$ is either monovalent $C_{10}$-$C_{36}$ alkyl (preferably monovalent $C_{18}$-$C_{30}$ alkyl), or monovalent α-hydroxy-$C_{10}$-$C_{36}$ alkyl (preferably monovalent α-hydroxy-$C_{18}$-$C_{30}$ alkyl); and
$R^4$ is $C_{10}$-$C_{20}$ alkyl.

Relative to the generic definition provided above, "ceramides," are those compounds of Formula I, wherein
X is H—;
$R^1$ is —(C=O)—;
$R^2$ is either —(CH=CH)— or —(CHOH)—$CH_2$—;
$R^6$ is alkyl or α-hydroxyalkyl; and
$R^4$ is $C_{10}$-$C_{20}$ alkyl.

Relative to the generic definition provided above, "ω-esterified ceramides" or "acylceramides," are those compounds of Formula I, wherein
X is H—;
$R^1$ is —(C=O)—;
$R^2$ is either —(CH=CH)— or —(CHOH)—$CH_2$—;
$R^3$ is alkanoyl with alkyl or α-hydroxyalkyl as both $R^5$ and $R^6$; and
$R^4$ is $C_{10}$-$C_{20}$ alkyl.

Relative to the generic definition provided above, "cerebrosides," are those compounds of Formula I, wherein
X is a monosaccharide;
$R^1$ is —(C=O)—;
$R^2$ is either —(CH=CH)— or —(CHOH)—$CH_2$—;
$R^3$ is alkyl or α-hydroxyalkyl; and
$R^4$ is $C_{10}$-$C_{20}$ alkyl.

Relative to the generic definition provided above, "ω-esterified cerebrosides" or "acylglycosyl sphingolipids" are those compounds of Formula I, wherein
X is an oligosaccharide, particularly a disaccharide;
$R^1$ is —(CO)—;
$R^2$ is either —(CH=CH)— or —(CHOH)—$CH_2$—;
$R^3$ is alkanoyl with alkyl or α-hydroxyalkyl as both $R^5$ and $R^6$; and
$R^4$ is $C_{10}$-$C_{20}$ alkyl.

Relative to the generic definition provided above, "ω-esterified cerebrosides" or "complex glycosphingolipids" are also those compounds of Formula I, wherein
X is a oligosaccharide, particularly a disaccharide;
$R^1$ is —(C=O)—;
$R^2$ is either —(CH=CH)— or —(CHOH)—CH$_2$—;
$R^3$ is alkyl or α-hydroxyalkyl; and
$R^4$ is $C_{10}$-$C_{20}$ alkyl, As used herein, the term "alkyl" refers to straight-chained or branched-chain groups that can be saturated (i.e., containing all single bonds) or unsaturated (i.e., containing one or more double bonds), and either monovalent or divalent as determined by their position within the structure provided as Formula I. In most instances, straight-chained alkyl groups are preferred in the disclosed formulations. Alkyl groups identified as "α-hydroxyalkyl" are derived from α-hydroxy fatty acids, with the α-position referring to the carbon adjacent to the carboxyl group involved in an ester or amide linkage.

The term "fatty acid residue" refers to the that portion of a fatty acid that remains after removal of the —COOH group.

Generally preferred classes of sphingolipids used in the disclosed formulations are those in which $R^1$ is —(C=O)— and $R^2$ is —(CH=CH)—.

Ceramides in the human stratum corneum play key physicochemical roles in establishing the barrier functions of the skin. The structures of those diverse ceramide species in the stratum corneum, had not been comprehensively described, until characterization by normal-phase liquid chromatography connected to electrospray ionization-mass spectrometry was conducted. These studies led to the discovery of a new ceramide class consisting of α-hydroxy fatty acid and dihydrosphingosine moieties, in addition to the 10 classes previously known. These studies revealed that the ceramides of the human stratum corneum comprise long-chain (more than $C_{18}$-containing) sphingoids and a great number of isobaric species (Masukawa, et al., Characterization of overall ceramide species in human stratum corneum. *J. Lipid Res.* 2008 July; 49:1466-76). The ceramide species identified in human stratum corneum by these studies include the following species:

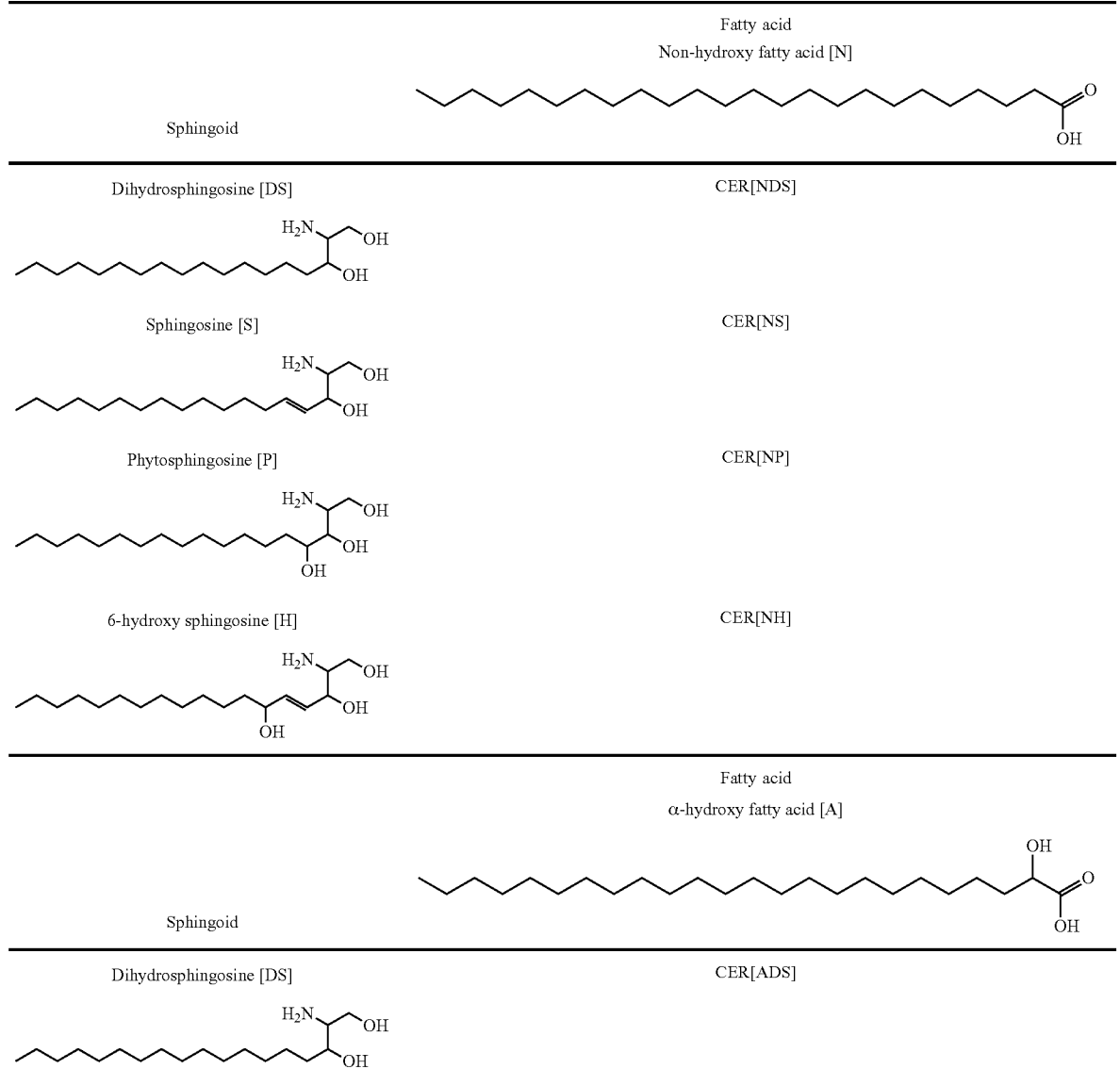

-continued

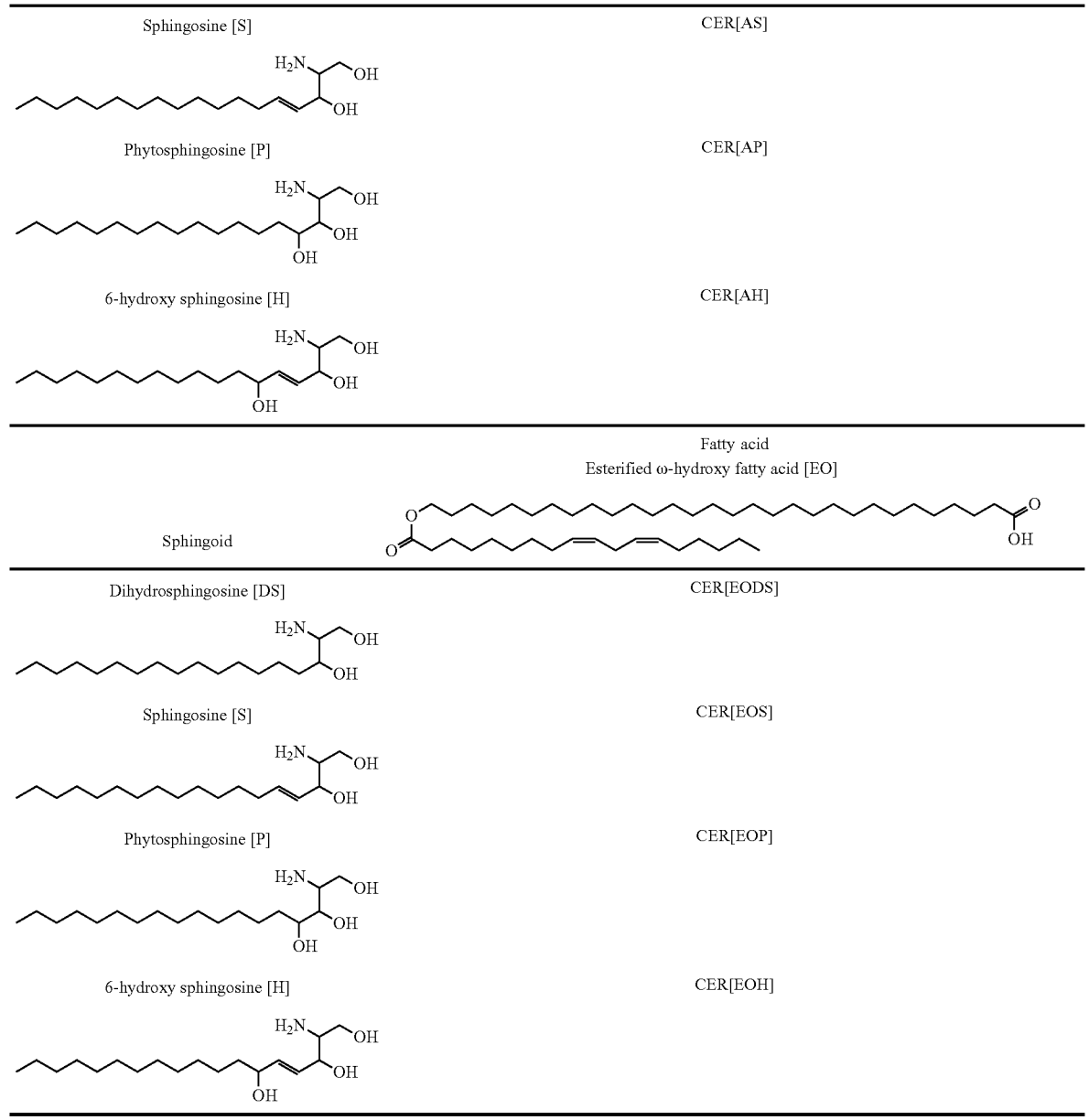

Source: Masukawa, et al., Characterization of overall ceramide species in human stratum corneum. *J. Lipid Res.* 2008 July; 49:1466-76.

The ceramides to be used in the disclosed formulations are chosen from at least one of the following: Cer 1 [EOS], Cer 2 [NS], Cer 3 [NP], Cer 4 [EOH], Cer 5 [AS], Cer 6 [AP], Cer 7 [AH], Cer 8 [NH], and Cer 9 [EOP], as identified in Holleran, et al., Epidermal sphingolipids: Metabolism, function and roles in skin disorders. *FEBS Lett.* 2006; 580:5456-66. The letter designations in the brackets (e.g., [EOS], [NS], and [NP]) of the ceramides listed immediately above, correspond to the same designations in brackets in the table above, such that, for example, "Cer 1 [EOS]" is the ceramide formed by an amide bond formed between the amino group of the sphingoid base, sphingosine, and the hydroxyl of the carboxylate group of the fatty acid, esterified ω-hydroxy fatty acid.

While not wishing to be bound by any one theory, it is believed that disruptions in the epithelial barrier caused by imbalances in the ceramide composition of the skin contribute to a variety of skin diseases and disorders. Consequently, the formulations of the present disclosure are designed to replenish particular ceramides that might be found in reduced concentrations in diseased skin, relative to healthy skin, in order to reestablish an appropriate balance of ceramides and other lipids within the skin. Additionally, in some embodiments, the formulations of the present disclosure are designed to activate the ceramide production pathways in the underlying layers of the skin, and thereby increase the overall content and alter the composition of ceramides in newly-formed skin.

In some embodiments the formulations of the present disclosure provide omega-hydroxy ceramides, because omega-hydroxy ceramides have been found to be deficient in diseased skin from patients suffering from atopic dermatitis. (Macheleidt, et al., Deficiency of epidermal protein-bound ω-hydroxyceramides in atopic dermatitis. *J. Invest. Dermatol.* 2002 July; 119(1):166-73.)

"Cholesterol esters," are cholesterol molecules having a fatty acid moiety attached through an ester bond. The ester bond is formed between the carboxylate group of the fatty acid and the hydroxyl group of cholesterol. As used herein, "lanosterol ester" refers to a fatty acid ester of lanosterol, wherein the ester bond is formed between the carboxylate group of a fatty acid and the free hydroxyl group of lanosterol. Exemplary cholesterol and lanosterol ("cholesterol and/or lanosterol") esters used in the disclosed formulations are those comprising fatty acids having between 10 and 30 carbons (i.e., $C_{10}$-$C_{30}$). In certain embodiments, commercial preparations of cholesterol/lanosterol esters are used as components of the disclosed formulations. Generally, such commercial preparations comprise a mixture of cholesterol/lanosterol esters comprising fatty acids of differing lengths. For example the commercial preparation known as "supersterol" comprises a mixture of $C_{10}$-$C_{30}$ cholesterol and/or lanosterol esters. Suitable cholesterol and/or lanosterol esters include, for example, cholesterol oleate, cholesterol laurate, cholesterol myristate, cholesterol palmitate, cholesterol stearate, cholesterol arachidate, cholesterol behenate, cholesterol lignocerate, cholesterol cerotate, cholesterol montanate, cholesterol melissate, lanosterol oleate, lanosterol laurate, lanosterol myristate, lanosterol palmitate, lanosterol stearate, lanosterol arachidate, lanosterol behenate, lanosterol lignocerate, lanosterol cerotate, lanosterol montanate, and lanosterol melissate.

Importantly, when a range of carbon atoms is presented, that range optionally includes all of the individual integers found between the limits of that range. For example, "$C_{10}$-$C_{20}$" optionally includes $C_{10}$, $C_{11}$, $C_{12}$, $C_{13}$, $C_{14}$, $C_{15}$, $C_{16}$, $C_{17}$, $C_{18}$, $C_{19}$ and $C_{20}$. However, that range can also be limited to only the even integers between the limits of that range. For example, "$C_{10}$-$C_{30}$" can optionally include only $C_{10}$, $C_{12}$, $C_{14}$, $C_{16}$, $C_{18}$, $C_{20}$, $C_{22}$, $C_{24}$, $C_{26}$, $C_{28}$, and $C_{30}$.

While not wishing to be bound by any one theory, it is believed that disruptions in the epithelial barrier caused by imbalance in the cholesterol and/or lanosterol ester composition of the skin, and particularly in relation to the non-esterified cholesterol and/or lanosterol composition of the skin, contribute to a variety of diseases and disorders. Consequently, the formulations of the present disclosure are designed to replenish particular cholesterol and/or lanosterol esters that are found in reduced concentrations in diseased skin, relative to healthy skin, in order to reestablish an appropriate balance of cholesterol and/or lanosterol esters with other lipids, and particularly non-esterified cholesterol and/or lanosterol within the epidermis. Moreover, the formulations of the present disclosure specifically exclude free cholesterol and/or lanosterol; since it has been shown that diseased skin from human patients suffering from atopic dermatitis and eczema have an overabundance of free cholesterol. (Di Nardo, et al., Ceramide and cholesterol composition of the skin of patients with atopic dermatitis. *Acta Derm. Venereol.* (Stockh) 1998; 78:27-30.)

Fatty acids are defined as "carboxylic acids with long aliphatic tails" and the aliphatic tails of naturally-occurring fatty acids may be saturated or unsaturated. The term "very long chain fatty acids," "VLC fatty acids" or "VLCFAs" refer to fatty acids having an aliphatic chain of more than 22 carbons. Exemplary VLCFAs include lignoceric acid ($C_{24}$), cerotic acid ($C_{26}$), montanic acid ($C_{28}$) and melissic acid ($C_{30}$). Such VLCFAs can be isolated from botanical sources, such as candelilla wax, obtained from the cuticle of the *Euphorbia cerifera* plant, or from other naturally-occurring sources, or can be chemically synthesized from smaller building block reactants. VLCFAs can also be isolated from beeswax, and such preparations can be used in the formulations or the present disclosure. However, such preparations of VLCFAs from beeswax can contain trace amounts of allergens, and are thus not preferred.

The suitability of free fatty acids to contribute to barrier function appears to depend on their chain length and their state of saturation, since both of these characteristics influence their ability to form highly ordered intercellular membrane structures (Small, D. M. Lateral chain packing in lipids and membranes, *J. Lipid Res.* 1984; 25:1490-1500). VLCFAs are highly hydrophobic and have a greater ability to prevent water loss than short chain fatty acids when incorporated into the lamellar phases of the stratum corneum. Saturated fatty acids are more resistant to oxidation than unsaturated fatty acids and are also able to align and form more highly ordered crystalline arrays at, skin temperature (Höltje et al., Molecular dynamics simulations of stratum corneum lipid models: fatty acids and cholesterol. *Biochem. Biophys. Acta* 2001; 1511:156-67). Modeling studies on VLCFAS and long chain ceramides suggest that these lipids more readily form crystalline arrays that are impermeable to water (Forslind, B. A domain mosaic model of the skin barrier. *Acta Derm. Venereol.* (Stockh) 1994; 74:1-6). Such crystalline arrays appear to be essential for effective barrier function, since this laterally-arrayed lipid organization is known to be altered in several skin diseases (Pilgram, et al., Aberrant lipid organization in stratum corneum of patients with atopic dermatitis and lamellar ichthyosis. *J. Invest. Dermatol.* 2001; 117:710-7).

While not wishing to be bound by any one theory, it is believed that disruptions in the epithelial barrier caused by imbalance in the fatty acid composition of the skin, contribute to a variety of diseases and disorders of the skin. Specifically, in certain diseases of the skin, such as atopic dermatitis or eczema, the epidermis appears to be deficient in VLCFAs, such as lignoceric acid ($C_{24}$), cerotic acid ($C_{26}$), montanic acid ($C_{28}$) and melissic acid ($C_{30}$), while having unchanged amounts, or in some cases, an excess of shorter-chained fatty acids, such as palmitic acid ($C_{16}$), oleic acid ($C_{18}$) and stearic acid ($C_{18}$). (Macheleidt, et al., Deficiency of epidermal protein-bound ω-hydroxyceramides in atopic dermatitis. *J. Invest, Dermatol.* 2002 July; 119(1):166-73.) Thus, it is believed that supplementation with VLCFAs is desired to reestablish or reinforce the epithelial barrier and thereby promote healthy skin. Consequently, the formulations of the present disclosure are designed to provide VLCFAs, such as lignoceric acid ($C_{24}$), cerotic acid ($C_{26}$), montanic acid ($C_{28}$) and melissic acid ($C_{30}$) to the epidermis.

"Isostearyl isostearate" refers to the isooctadecyl ester of isooctadecanoic acid (also known as stearic acid), having the molecular formula of $C_{36}H_{72}O_2$ and the following structure:

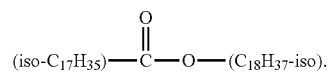

Isostearyl isostearate is a representative of a class of compounds formed by linking a fatty alcohol to a fatty acid through an ester bond, which can generally be referred to as "fatty esters of fatty acids," or "FEFAs." Although the embodiments the formulations disclosed herein specifically comprise isostearyl isostearate, it should be recognized that other FEFAs can be used in place of, or in addition to, isostearyl isostearate. When alternative FEFAs are used in the disclosed formulations, they should contain approximately the same number of carbons as isostearyl isostearate, such as for example $C_{32}$, $C_{33}$, $C_{34}$, $C_{35}$, $C_{36}$, $C_{37}$, $C_{38}$, $C_{39}$ and $C_{40}$, with approximately half of the carbons residing in the aliphatic chain of the fatty alcohol and approximately half in the aliphatic chain of the fatty acid.

While not wishing to be bound by any one theory, it is believed that isostearyl isostearate, and related FEFAs, when topically applied, can effectively promote a healthy epidermal barrier and reduce trans-epidermal water loss (TEWL) by promoting tighter packing of the lipids within the skin, thereby promoting internal occlusion of water, See: Pennick, et al., Superior effect of isostearyl isostearate on improvement in stratum corneum water permeability barrier function as examined by the plastic occlusion stress test. *Int. J. Cosm. Sci.* 2010 August; 32(4): 304-12 and Dederen, et al., Emollients are more than sensory ingredients: the case of Isostearyl Isostearate, *Int. J. Cosm. Sci.* 2012; 34: 502-10.

"Phytosphingosine," which is also known as "4-D-hydroxysphinganine" refers to a species of sphingoid base having the molecular formula of $C_{18}H_{38}NO_3$, and the structure:

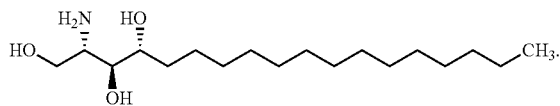 [SMILES: CCCCCCCCCCCCCC[C@@H](O)[C@@H](O)[C@@H](N)CO]

N-Stearoyl-phytosphingosine is a sphingolipid comprising the $C_{18}$ fatty acid, octadecanoic acid (also known as stearic acid) and phytosphingosine, wherein in the carboxyl group of octadecanoic acid forms an amide bond with the amine of phytosphingosine. N-Stearoyl-phytosphingosine has the molecular formula $C_{36}H_{73}NO_4$, and the structure:

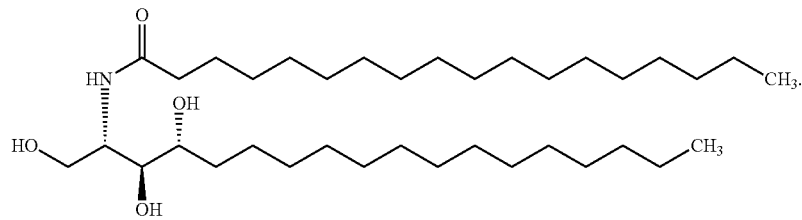 [SMILES: CCCCCCCCCCCCCCCCCC(=O)N[C@@H](CO)[C@H](O)[C@H](O)CCCCCCCCCCCCCC]

It has been demonstrated that when applied to the skin of mice, N-stearoyl-phytosphingosine and phytosphingosine effectively inhibited histamine-induced scratching behavior. These studies further revealed that these compounds inhibited the expression of the allergic cytokines, IL-4 and TNF-alpha, and inhibited the activation of the transcription factors, NF-kappaB and c-jun, in histamine-stimulated skin. Further, both compounds were shown to exhibit potent anti-histamine effects in the Magnus test using guinea pig ileum, an art-accepted model for testing anti-histamine activity. Ryu, et al., Anti-scratching behavior effects of N-stearoyl-phytosphingosine and 4-hydroxysphinganine in mice. *Lipids.* 2010 July; 45(4613-8.

While not wishing to be bound by any one theory, it is believed that incorporation of N-stearoyl-phytosphingosine and phytosphingosine into the disclosed formulations will inhibit the expression of IL-4 and TNF-alpha, and will also exhibit anti-histamine and anti-inflammatory activity, when topically applied to human skin.

Additionally, phytosphingosine, and other sphingoid bases and fatty acids are known to poses antibacterial and antimycotic activity (Fischer, et al., Antibacterial activity of sphingoid bases and fatty acids against Gram-positive and Gram-negative bacteria. *Antimicrob. Agents Chemother.* 2012 March; 56(3):1157-61 and Veerman, et al., Phytosphingosine kills *Candida albicans* by disrupting its cell membrane, *Biol. Chem.* 2010 January; 391(1):65-71.), Hence, while not wishing to be bound by any one theory, phytosphingosine is included in some embodiments of the disclosed formulations to inhibit the growth of undesired, or pathogenic, Gram-positive and Gram-negative bacteria, such as *Staphylococcus aureus*, as well as *Candida albicans*, and other pathogenic fungi. In other embodiments of the disclosed formulations, D-sphingosine, dihydrosphingosine, or the fatty acid, lauric acid, or combinations thereof, including combinations with phytosphingosine, can be used to limit the growth of undesired, or pathogenic, Gram-positive and Gram-negative bacteria, such as *Staphylococcus aureus*, as well as *Candida albicans*, and other pathogenic fungi.

"Hydrocortisone," which is also known as "cortisol," is a steroid hormone, and more specifically a glucocorticoid, normally produced by the zona fasciculata of the adrenal cortex of mammals. It is released in response to stress and low levels of blood glucocorticoids, and it primarily functions to increase blood sugar through gluconeogenesis; suppress the immune system; and aid in fat, protein and carbohydrate metabolism. Synthetic forms of cortisol, and closely-related analogs, have been used to treat a variety of diseases. Hydrocortisone and its analogs act by down-regulating the interleukin-2 receptor (IL-2R) on "helper" ($CD4^+$) T-cells, resulting in the inability of interleukin-2 to up-regulate the Th2 (humoral) immune response, which results in a Th1 (cellular) immune dominance, and a decrease in B-cell antibody production. Hence, when administered to a mammal, cortisol prevents the release of substances in the body that cause inflammation. Consequently, cortisol is used to treat conditions resulting from overactivity of the B-cell mediated antibody response, as seen in inflammatory diseases, rheumatoid diseases, and allergies.

In some embodiments of the disclosed formulations hydrocortisone, or an analog thereof, including, for example, the synthetic glucocorticoids kenelog/triamcinolone, clobetasol, betamethasone, fluticasone, fluocinonide, etc., or combinations thereof, are incorporated as an anti-inflammatory agent. Such embodiments of the disclosed formulations are intended for use on diseased skin exhibiting an inappropriate or excessive inflammatory response. Such embodiments of the disclosed formulations are also intended for use on the skin of subjects exhibiting allergic dermatitis, or other diseases or disorders that involve an inappropriate or excessive response to an exogenous or endogenous allergen.

"Glycyrrhetinic acid" is a pentacyclic triterpenoid derivative of the beta-amyrin type obtained from the hydrolysis of glycyrrhizic acid (glycyrrhizin).

Glycyrrhizic acid has the structure:

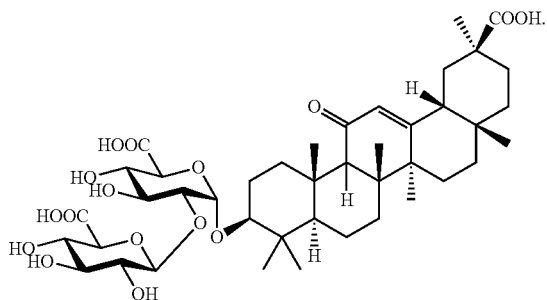

While glycyrrhetinic acid, and particularly 18β-glycyrrhetinic acid, has the structure:

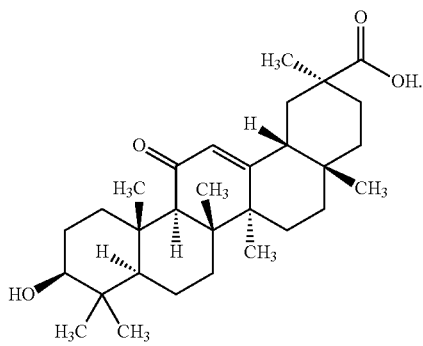

18β-Glycyrrhetinic acid is the major metabolite of glycyrrhizic acid, and is an important constituent of licorice and licorice root. Glycyrrhetinic acid can be chemically synthesized or can be obtained by extraction from licorice root. Although it is used as a flavoring, and it masks the bitter taste of drugs like aloe and quinine, 18β-glycyrrhetinic acid is also known to have a variety of other activities. (Krähenbühl, et al., Kinetics and dynamics of orally administered 18β-glycyrrhetinic acid in humans. *J. Clin. Endocrinol. Metab.* 1994 March; 78(3):581-5).

Moreover, both glycyrrhizic acid and 18β-Glycyrrhetinic acid have been shown to exhibit corticosteroid like anti-inflammatory and anti-allergic activity. These compounds apparently act indirectly by potentiating the activity of corticosteroids. In vitro, glycyrrhetinic acid is known to inhibit Δ4β-reductase, an enzyme that competitively inactivates steroid hormones, and 11β-hydroxysteroid dehydrogenase, the enzyme that deactivates cortisol (Hikino H. Recent research on Oriental medicinal plants. In: Wagner H, Hikino H, Farnsworth N R, eds. *Economic and medicinal plant research*. Vol, 1. London, Academic Press, 1985:53-85.). Glycyrrhizin given intraperitoneally has been shown to suppress contact dermatitis in mice, and was found to be more effective than prednisolone, but is ineffective when administered orally (Bradley P R, ed. *British herbal compendium, Vol.* 1. Bournemouth, British Herbal Medicine Association, 1992; 145-148.).

In vitro, glycyrrhizic acid has been shown to inhibit the growth of *Staphylococcus aureus, Mycobacterium smegmatis*, and *Candida albicans* (Mitscher L A et al., Antimicrobial agents from higher plants. Antimicrobial isoflavanoids and related substances from *Glycyrrhiza glabra* L. var. typica. *J. Natural Products,* 1980; 43:259-269).

Carbenoxolone is a synthetic derivative of glycyrrhetinic acid, also inhibits 11β-hydroxysteroid dehydrogenase, as does chenodeoxycholic acid (Diederich, et al., In the search for specific inhibitors of human 11β-hydroxysteroid dehydrogenase (11β-HSDs): chenodeoxycholic acid selectively inhibits 11β-HSD-I. *Euro. J. Endocrinol.* 2000 February; 142(2): 200-7) (Cheng, et al., The development and SAR of pyrrolidine carboxamide 11beta-HSD1 inhibitors, *Bioorg. Med. Chem. Lett.* 2010 May 1; 20(9) 2897-902) and PF-877423 (Johansson, et al., 2-Amino-1,3-thiazol-4(5H)-ones as potent and selective 11beta-hydroxysteroid dehydrogenase type 1 inhibitors: enzyme-ligand co-crystal structure and demonstration of pharmacodynamic effects in C57Bl/6 mice. *J. Med. Chem.* 2008 May 22; 51(10):2933-43). Consequently, carbenoxolone, chenodeoxycholic acid, and PF-877423, and combinations thereof, can be used in place of, or in combination with 18β-glycyrrhetinic acid and/or glycyrrhizic acid in the disclosed formulations.

While not wishing to be bound by any one theory, it is believed that formulations comprising 18β-glycyrrhetinic acid, glycyrrhizic acid, carbenoxolone, chenodeoxycholic acid, or PF-877423, or combinations thereof, can be therapeutically beneficial in repairing and restoring a healthy epidermal barrier due to the activities identified above. In particular, the demonstrated antibacterial activities of 18β-glycyrrhetinic acid and/or glycyrrhizic acid against *Staphylococcus aureus, Mycobacterium smegmatis*, and *Candida albicans* suggest that therapeutic amounts of these compounds can be used to reduce the amount of such pathogens on or in epidermal tissues. Moreover, it is believed that topical or parenteral administration of 18β-glycyrrhetinic acid, glycyrrhizic acid, carbenoxolone, chenodeoxycholic acid, or PF-877423, or combinations thereof, can potentiate the activity of simultaneously or subsequently administered corticosteroids. Consequently, in one aspect, the disclosed formulations comprise a combination of 18β-glycyrrhetinic acid, glycyrrhizic add, carbenoxolone, chenodeoxycholic acid, or PF-877423, or combinations thereof, and a corticosteroid, such as cortisol (i.e., hydrocortisone) or an analog thereof, including, for example, the synthetic glucocorticoids kenelog/triamcinolone, clobetasol, betamethasone, fluticasone, fluocinonide, etc., or combinations thereof, in a pharmaceutically acceptable carrier. In another aspect the disclosed formulations comprise a combination of 18β-glycyrrhetinic add, glycyrrhizic acid, carbenoxolone, chenodeoxycholic acid, or PF-877423, or combinations thereof, and a corticosteroid in the presence of a therapeutic composition comprising specific sphingolipids, cholesterol esters, very long chained fatty acids, and, optionally, fatty alcohol esters of fatty acids, as disclosed herein.

"Niacinamide," which is also known as "nicotinamide" and "nicotinic acid amide" refers to the amide of nicotinic acid (or vitamin $B_3$ or niacin). Niacinamide has been shown to decrease transepidermal water loss in atopic dermatitis and has been shown to be a more effective moisturizer than white petrolatum on atopic dry skin (Soma, et al., Moisturizing effects of topical nicotinamide on atopic dry skin. *Int. J. Dermatol,* 2005 March; 44(3):197-202). Mechanistically, niacinamide has been shown to improve the epidermal permeability barrier by stimulating the de novo synthesis of ceramides (e.g., glucosylceramide and sphingomyelin) through up-regulated expression of serine palmitoyltransferase—the rate-limiting enzyme in sphingolipid synthesis (Tanno, et al., Nicotinamide increases biosynthesis of ceramides as well as other stratum corneum lipids to improve the epidermal permeability barrier. *Br. J. Dermatol.* 2000 September; 143(3): 523-31). Niacinamide also has demonstrated anti-inflammatory activity that may be of benefit to patients with inflammatory skin conditions (Niven. Pharmacologic doses of nicotinamide in the treatment of inflammatory skin conditions: a review. *Cutis* 2006 January; 77(1 Suppl): 11-6), including such conditions as acne vulgaris and atopic dermatitis. Moreover, niacinamide can suppress antigen-induced, lymphocytic transformation and inhibit. 3'-5' cyclic AMP phosphodiesterase, and also has demonstrated ability to block the inflammatory actions of iodides known to precipitate or exacerbate inflammatory acne (Shalita, et al., Topical nicotinamide compared with clindamycin gel in the treatment of inflammatory acne vulgaris. *Int. J. Dermatol.* 1995 June; 34(6):434-7).

While not wishing to be bound by any one theory it is believed that the inclusion of niacinamide in the disclosed formulations can provide synergistic therapeutic benefits that ultimately result from these demonstrated activities of niacinamide. In particular, it is believed that niacinamide, in combination with 18β-glycyrrhetinic acid, glycyrrhizic acid, carbenoxolone, chenodeoxycholic acid, or PF 877423, or combinations thereof, and optionally in the presence of a corticosteroid, such as cortisol (i.e., hydrocortisone) or an analog thereof, including, for example, the synthetic glucocorticoids kenelog/triamcinolone, clobetasol, betamethasone, fluticasone, fluocinonide, etc., or combinations thereof, can provide synergistic therapeutic benefits when such ingredients are provided topically in a simple combination, or in combination with the formulations of sphingolipids, cholesterol esters, very long chained fatty acids, and, optionally, fatty alcohol esters of fatty acids disclosed herein. It is further believed that such combinations of niacinamide and 18β-glycyrrhetinic acid, glycyrrhizic acid, carbenoxolone, chenodeoxycholic acid, or PF-877423, or combinations thereof, and optionally a corticosteroid, such as cortisol (i.e., hydrocortisone) or an analog thereof, including, for example, the synthetic glucocorticoids kenelog/ triamcinolone, clobetasol, betamethasone, fluticasone, fluocinonide, etc., or combinations thereof, when provided topically in a simple combination, or in combination with the formulations of sphingolipids, cholesterol esters, very long chained fatty acids, and, optionally, fatty alcohol esters of fatty acids disclosed herein, can be used to treat epidermal barrier defects, to repair, replenish or maintain an effective epidermal barrier, and/or to treat a variety of dermatological disease and disorders associated with such epidermal barrier defects.

The normal pH on the surface of healthy adult skin is acidic, due to the components of the stratum corneum, sebum and sweat secretion. Indeed, careful studies have found that the 'natural' skin surface pH is on average 4.7, i.e., below 5 (Lambers, et al., Natural skin surface pH is on average below 5, which is beneficial for its resident flora. *Int. J. Cosmet. Sci.* 2006 October; 28(5):359-70). The acidic pH of the horny layer of the stratum: corneum is referred to the 'acid mantle,' and is important for cutaneous antimicrobial defense, through maintenance of naturally-occurring, resident skin flora. In diseased skin this 'acid mantle' is often compromised, and the pH of the skin can be neutral to slightly alkaline. Shifts in the pH of the skin are known to affect the microbiome of the skin, and alkaline pHs can allow for or even promote the growth of undesired or pathogenic microorganisms. Restoring the normal acid mantle of the skin is promotes healthy skin by supporting the growth of protective microbiota found on healthy skin, while inhibiting the growth of microorganisms characteristically found on diseased skin (Id.).

Moreover, the pH of the skin follows a gradient across the horny layer (from less than 5.0 at the surface to neutral in the basal layers), thereby influencing the activities of the pH-dependent enzymes that regulate skin cornification, desquamation and homeostasis of barrier function. These enzymes—beta glucocerebrosidase and acidic sphingomyelinase—are essential for ceramide production, lipid processing and lamellar formation and secretion, and are known to have pH optima of around 5.0 (Vaccaro, et al., Characterization of human glucosylsphingosine glucosyl hydrolase and comparison with glucosylceramidase. *Eur. J. Biochem.* 1985 Jan. 15: 146(2); 315-21; Takagi, et al., Beta-glucocerebrosidase activity in mammalian stratum corneum. *J. Lipid Res.* 1999 May; 40(5):861-9). Additionally, in a neutral or alkaline environment, beta-glucocerebrosidases and acid sphingornyelinases are inactivated and metabolized by epidermal serine proteases, which have pH optima in the neutral-to-alkaline range. Consequently, formation of the lamellar extracellular arrangement of barrier lipids requires an acidic milieu.

Endogenous and exogenous factors affect the acidity of the skin, with the most important factors being age, anatomic site, the use of detergents (soaps or synthetic detergents) and cosmetic products, occlusion by body folds or dressings, skin irritants and the use of topical pharmacological substances (Schmid-Wendtner and Korting. The pH of the skin surface and its impact on the barrier function. *Skin Pharmacol. Physiol.* 2006; 19(6): 296-302).

Changes in skin pH can play a role in the pathogenesis, prevention and treatment of irritant contact dermatitis, atopic dermatitis, ichthyosis, rosacea, acne vulgaris, *Candida albicans* infections and wound healing. The acidity of the skin surface is thought to be bacteriostatic for some pathogens since many prefer to grow at a neutral pH. A correlation between pH and bacterial growth has been described for propionibacteria after the use of alkaline soap on the forehead (Korting, et al., Influence of repeated washings with soap and synthetic detergents on pH and resident flora of the skin of forehead and forearm. Results of a cross-over trial in health probationers. *Acta Derm Venereol* 1987; 67(1): 41-7) and for the development of mycoses in skin folds in patients with diabetes and patients on dialysis (Yosipovitch, et al., Skin surface pH in intertriginous areas in NIDDM patients. Possible correlation to candidal intertrigo. *Diabetes Care* 1993; 16(4): 560-3).

In view of the importance of pH on the health of the skin and the intactness of the epidermal barrier, the disclosed formulations are designed to maintain a pH as close to the range of 4.6 to 5.6 as possible. These pH values are in the range of optimal activity of beta-glucocerebrosidase and acid sphygomyelinase and in the range of a healthy epidermal barrier. A disrupted epidermal barrier has an abnormally alkaline pH which leads to the serine protease mediated inactivation and metabolism of the beta-glucocerebrosidase and acid sphingomyelinase enzymes, which are responsible for the production of ceramides. The disrupted, alkaline skin barrier is also unable to support a healthy microbiome, since it promotes the growth of harmful bacteria like *Staphylococcus aureus* and *Propionibacterium acnes*, while inhibiting the growth of "friendly" bacteria such as *Staphylococcus epidermidis*. This shift in the microbiome of the skin leads to the cycle of increased alkalinity, superinfection of pathogenic bacteria, and a disrupted epidermal barrier.

Although the acid dissociation constants of citric and lactic acids are such that citrate and lactate buffers can be used to maintain appropriately-acidic pHs, these organic acids are not ideal for use in the disclosed formulations because they can readily crystallize, forming crystals that irritate the skin, and can readily form addition salts that can also readily crystallize, forming crystals that can irritate the skin. Consequently, in most embodiments, citric acid and lactic acid are not used as acidifying agents in the disclosed formulations. Instead, glucono delta-lactone, lactobionic acid, or α-hydroxyacids, β-hydroxyacids, or other polyhydroxy acids, or combinations thereof, are used as preferred acidifying agents to lower the pH of the formulations to the desired range of 4.6 to 5.6.

"Glucono delta-lactone," which is also known as "gluconolactone," "D-Glucono-1,5-lactone," "1,5-D-gluconolactone," "1,5-delta-gluconolactone," "D-Gluconic acid δ-lactone," or "GDL," refers to a lactone (cyclic ester) or oxidized derivative of D-Gluconic acid, with the following structure:

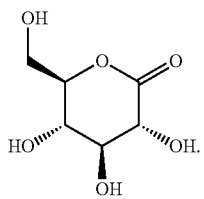

Gluconolactone is a polyhydroxy acid (PHA) that is capable of chelating metals and may also scavenge free radicals. When dissolved in water, it is partially hydrolyzed to gluconic acid, with the balance between the lactone form and the add form established as a chemical equilibrium. Gluconic acid is a noncorrosive, nonvolatile, nontoxic, mild organic acid with a pKa of 3.7 (Ramachandran et al., Gluconic Acid: A Review. *Food Technol. Biotechnol.* 2006; 44(2); 185-95.). On account of these properties, glucono delta-lactone is used as both a "sequestrant" and an "acidifier" in foods. "Sequestrants," a term generally used in the context of food additives, improve the quality and stability of the food products by forming chelate complexes with metal ions, especially copper, iron and nickel ions, which otherwise serve as catalysts in the oxidation of the fats in the food. In particular, by chelating free iron ions, glucono delta-lactone blocks the formation of hydroxyl radicals, thereby serving as an antioxidant.

In addition, glucono delta-lactone is also known to have photoprotective activity (Bernstein, et al., The polyhydroxy acid gluconolactone protects against ultraviolet radiation in an in vitro model of cutaneous photoaging. *Dermatol. Surg.* 2004 February; 30(2 Pt 1):189-95), and, as an alpha hydroxyacid, glucono delta-lactone, is known to enhance stratum corneum desquamation, improve skin appearance, and prevent skin irritation (Berardesca et al., Alpha hydroxyacids modulate stratum corneum barrier function. *Br. J. Dermatol.* 1997 December; 137(6):934-8). Consequently, glucono delta-lactone is utilized as an acidifying agent in some embodiments of the disclosed formulations for its ability to acidify the skin, protect the skin from damage by ultraviolet radiation, lessen or prevent irritation, enhance desired stratum corneum desquamation, and improve skin appearance. In some embodiments, glucono delta-lactone is used in combination with lactobionic acid.

Lactobionic acid, which is also known as "4-O-β-galactopyranosyl-D-gluconic acid," or "galactosylgluconic acid," is a "sugar acid," and is technically a disaccharide formed from gluconic acid and galactose with the following structure:

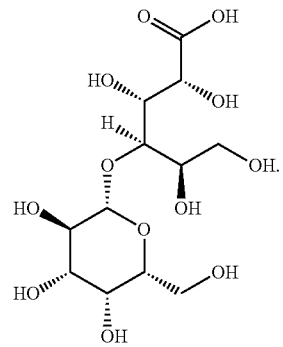 [SMILES: O=C(O)[C@H](O)[C@@H](O)[C@H](O[C@@H]1O[C@H](CO)[C@H](O)[C@H](O)[C@H]1O)[C@H](O)CO]

Lactobionic acid has a pka of 3.8. Like glucono delta-lactone, because lactobionic acid possesses multiple hydroxyl functional groups, it can act as a metal ion chelator, or sequestrant. Like glucono delta-lactone, when chelating iron in particular, lactobionic acid inhibits the production of hydroxyl radicals, thereby functioning as an antioxidant. Additionally, pure lactobionic acid is hygroscopic and forms a gel containing about 14% water from atmospheric moisture. (Draelos. Procedures in Cosmetic Dermatology Series: Cosmeceuticals. Elsevier Health Sciences, Oct. 31, 2008; 256 pp.) Consequently, lactobionic acid is used as an acidifying agent in some embodiments of the disclosed formulations, either atone or in combination with glucono delta-lactone.

Although glucono delta-lactone and lactobionic acid are specifically named as acidifying agents for use in the presently disclosed formulations, other acidifying agents can be utilized in these formulations, either in place of, or in combination with glucono delta-lactone and/or lactobionic acid. In some embodiments, either an α-hydroxyacid, a β-hydroxyacid, or another polyhydroxy acid, or any combination thereof, can be used in the disclosed formulations, either in place of, or in combination with glucono delta-lactone and/or lactobionic acid. The advantages of particular hydroxyacids for clinical and cosmeceutical use are well documented, and the use of such hydroxyacids in particular embodiments of the disclosed formulations is contemplated. (See Green et al., Clinical and cosmeceutical uses of hydroxyacids. *Clin. Dermatol.* 2009 September-October; 27(5):495-501.

Ethylenediaminetetraacetic acid (EDTA) is also a sequestrant, and is often used to improve the stability of personal care products (shampoos and cosmetics). Its effectiveness lies in its ability to function as a hexadentate ("six-toothed") ligand and chelating agent, "sequestering" metal ions such as $Ca^{2+}$ and $Fe^{3+}$. In some embodiments of the disclosed formulations, a calcium chelator, such as EDTA or phytic acid is used as a sequestrant or preservative, or to specifically alter the calcium gradient known to exist in healthy skin.

The amount of EDTA used in the presently disclosed formulations is carefully chosen to provide sufficient chelation ability to remove calcium from the outermost layers of the stratum corneum, and to encourage the formation of a calcium gradient reminiscent of that of healthy skin, in which calcium concentrations gradually increase through the stratum basale and the stratum spinosum, to reach a peak in the outer stratum granulosum, before diminishing through the stratum lucidum and stratum corneum. It is believed that this characteristic calcium gradient in the epidermis is important for permeability barrier homeostasis, epidermal cell differentiation, and regulating desquamation of corneocytes at the surface of the skin (Elias, et al., Origin of the epidermal calcium gradient: Regulation by barrier status and role of active vs passive mechanisms. *Invest. Dermatol.* 2002; 118:1269-1274). While not wishing to be bound by theory, it is believed that the use of EDTA in the disclosed formulations can help establish a calcium gradient reminiscent of that found in healthy skin, and thereby support permeability barrier homeostasis, epidermal cell differentiation, and the proper desquamation of corneocytes at the surface of the skin.

Additionally, by chelating free iron ions, EDTA blocks the formation of hydroxyl radicals, thereby serving as an antioxidant.

Additional Ingredients:

Provided herein are exemplary formulations comprising different subsets of ingredients selected from the chemical moieties described above, and additional ingredients as described below. In some embodiments these formulations are intended for topical administration to the skin and/or mucous membranes of mammalian subjects, and particularly humans, in need of such treatment.

In addition to the ingredients described above, as would be appreciated by the artisan skilled in the preparation of formulations designed for topical application to the skin, the disclosed formulations can also contain a wide variety of dermatologically acceptable diluents or vehicles, thickeners, humectants, emulsifiers, emollients, structure agents, conditioning agents, antioxidants, preservatives and pH adjusters. The list below is not meant to be fully inclusive or limiting, but is provided as a general guide. Example diluents or vehicles include water, dermatologically acceptable alcohols, petrolatum, or combinations thereof. Dermatologically acceptable alcohols can be selected from the simple short-chain alcohols and the toxicologically safe polyols. Examples include ethanol, isopropanol, propylene glycol, and glycerol. Especially preferred is a member selected from the group consisting of ethanol, isopropanol, and mixtures thereof. Example thickeners include gums, such as xantham gum. Example humectants include propanediol and glycerin. Example emulsifiers include glyceryl stearate, cetyl alcohol, polyglyceryl-10 pentastearate, behenyl alcohol and sodium stearoyl lactylate, and combinations thereof. Example emollients include petrolatum, caprylic/capric triglyceride, and isostearyl isostearate. Example structural agents include waxes, such as *Euphorbia cerifera* (Candelilla) wax, beeswax, Chinese Wax and paraffin wax. In some embodiments, waxes, such as *Euphorbia cerifera* (Candelilla) wax, beeswax, Chinese wax and paraffin wax, and VLCFAS can serve as both structure agents and skin conditioning agents. Example conditioning agents include $C_{10}$-$C_{30}$ cholesterol esters. Example antioxidants include BHT (butylated hydroxytoluene) and BHA (butylated hydroxyanisole), tocopherols, such as Vitamin E derivatives, and propyl gallate. Example preservatives include gluconolactone, gluconic acid, EDTA, 1,2-hexanediol, and caprylyl glycol.

The disclosed formulations can also include, for example, any other ingredients know to be effective for application to the epidermis, and particularly ingredients that are known to not be irritants or cause any allergic reactions when applied to the skin.

Alternative Combinations of Components of the Disclosed Formulations:

In particular embodiments, the disclosed formulations contain combinations of specific subsets of the components disclosed above. For example, the disclosed formulation may contain, at minimum, combinations of two, three, tour, five, or more of the following components: gluconolactone and/or lactobionic acid; niacinamide; 18β-glycyrrhetinic acid and/or glycyrrhizic acid; one or more sphingolipids, including, for example, ceramide 3 (i.e., "CER[NP]"); one or more cholesterol esters; one or more VLCFAs; isostearyl isostearate; phytosphingosine; one or more glucocorticoid, including hydrocortisone and/or an analog thereof; and EDTA. For example, in some embodiments the formulations can comprise a combination of gluconolactone, niacinamide, and 18β-glycyrrhetinic acid. In other embodiments the formulations can comprise a combination of gluconolactone, niacinamide, 18β-glycyrrhetinic acid, and a sphingolipid, such as ceramide 3. In still other embodiments the formulations can comprise a combination of gluconolactone, niacinamide, 18β-glycyrrhetinic acid, a sphingolipid, such as ceramide 3, and a glucocorticoid. Such formulations can also contain any combination of dermatologically acceptable diluents or vehicles, thickeners, humectants, emulsifiers, emollients, structure agents, conditioning agents, antioxidants, preservatives and/or pH adjusters, sufficient to impart the desired physical characteristics on the final formulation.

In some embodiments the combinations of components used in the formulation are specifically chosen for topical administration. In some embodiments the components are specifically chosen for treating a particular disease or disorder. When "combination approaches" are used for treatment of a particular disease or disorder, particular combinations of components may be chosen for topical administration, while other combinations of components may be chosen for oral, intralesional, or parenteral administration. When such "combination approaches" are used for treatment of a particular disease or disorder, the combination of components chosen for topical administration, and the combination of components chosen for oral, intralesional, or parenteral administration, are carefully selected such that the formulation for topical administration is therapeutically complementary to the formulation for oral or parenteral administration.

Dosage Forms and Packaging:

The disclosed formulations can take various forms. For example, the disclosed formulations for topical administration can be in the form of ointments, lotions, creams, foams, gels, solutions or sprays. The disclosed formulations can also be incorporated into dedicated applicators, such as saturated pads, to facilitate administration to the skin. When "combination approaches" are used for treatment of a particular disease or disorder, the formulations for topical administration will generally be different from the formulations for oral, intralesional, or parenteral administration.

The disclosed formulations may be packaged to provide a single dose or multiple doses and to provide a convenient means of transport, handling, and administration. The disclosed formulations may also be packaged in such a way as to protect the formulation from oxidation, bacterial contamination, or other forms of deterioration or degradation. For example, the disclosed formulations for topical administration can be packaged into crimped tubes, airless containers, or sealed foil-lined packets, which may optimally contain enough of the formulation for a single application, or a limited number of applications. Whereas, the formulations for oral or parenteral administration can be packaged in any suitable container. The disclosed formulations for topical administration can be packaged in larger containers designed for multiple applications. When packaged in such larger containers, those containers may be equipped with pumps or other mechanisms designed to facilitate the delivery of an appropriate volume of the formulation, while reducing the likelihood of contamination or oxidation.

Ointment Formulations:

In some embodiments the disclosed formulations for topical administration are ointments. Ointments are generally defined as formulations lacking any aqueous materials.

The ointment formulations of the present disclosure comprise combinations of different types of waxes in addition to the components described more fully above. In some embodiments, the ointment formulations of the present disclosure comprise a combination of microcrystalline wax, a VLCFA, and paraffin.

Microcrystalline waxes are a type of wax produced during the petroleum refining process by de-oiling petrolatum. In contrast to the more familiar paraffin wax which contains mostly unbranched alkanes, microcrystalline wax contains a higher percentage of isoparaffinic (branched) hydrocarbons and naphthenic hydrocarbons, and consists of high molecular weight saturated aliphatic hydrocarbons. As its name microcrystalline wax is characterized by the fineness of its crystals relative to the larger crystals of paraffin wax. Microcrystalline wax is generally darker, more viscous, denser, tackier and more elastic than paraffin waxes, and has both a higher molecular weight and melting point. The elastic and adhesive characteristics of microcrystalline waxes are related to the non-straight chain components which they contain, Typical microcrystalline wax crystal structure is small and thin, making them more pliable than paraffin wax.

Paraffin wax is a white or colorless soft solid derived from petroleum that consists of a mixture of hydrocarbon molecules containing between twenty and forty carbon atoms. It is solid at room temperature and begins to melt above approximately 37° C. (99° F.); with a boiling point of >370° C. (698° F.).

The ratio of microcrystalline wax, to VLCFA, to paraffin used in the ointment formulations disclosed herein is chosen to control the physical properties of the final ointment formulation. The physical properties influenced by the ratio of microcrystalline wax, to VLCFA, to paraffin include the viscosity and melting temperature of the final ointment formulation. The viscosity must be sufficiently thick at room temperature to promote ease of handling. Ointments having too great viscosity (i.e., overly "thick" ointments) can be difficult to expel or extrude from the containers in which they are routinely stored, such as a crimped tube. Generally ointments having too great viscosity at room temperature present even greater problems at colder temperatures (i.e., at temperature below room temperature). Ointments having too little viscosity (i.e., overly "thin" ointments) can be difficult to handle or apply due to their more liquid consistency. Generally ointments having too little viscosity present even greater problems at warmer temperatures (i.e., such as temperature above room temperature). The melting temperature of the final ointment formulation greatly influences the ease in handling and the ease in applying these formulations. The melting temperature of the final ointment formulation also influences the feel of the ointment formulation on the skin, after it has been applied. An overly viscous formulation can feel greasy or sticky. Ideally the ointment formulations of the present disclosure liquefy once applied to the skin, as a result of the warmth of the skin to which the ointment formulation is applied.

All of the formulations for topical administration according to the present disclosure can also comprise ceramides. Both the type and the amount of ceramide included in the formulation may be altered or adjusted to adapt the formulation for specific therapeutic objectives. In the ointment formulations of the present disclosure, ceramide 3 is used as a skin conditioning agent, along with phytosphingosine. The ratio of the ceramide 3 and phytosphingosine to the various waxes used in the formulation is also chosen carefully to create an ointment formulation with the desired physical properties, as outlined above for the wax components of the formulations. The ratio of ceramides and phytosphingosine to waxy components is also chosen to insure that the ceramides and phytosphingosine stay solubilized in the final ointment preparation. The method of manufacture outlined in the Examples below was chosen to fully solubilize the ceramides and phytosphingosine, and maintain them in a solubilized state, without damaging these components through thermal stress. There are, however, many other ways of solubilizing ceramides and phytosphingosine that the artisan skilled in the art of preparing dermatological formulations might employ. Such methods of solubilizing ceramides are contemplated for use in preparing the formulation disclosed herein.

Aspects of the Disclosed Formulations:

In a first aspect, the disclosed formulations for topical administration are compositions comprising therapeutically effective amounts of at least one of each of the following:
a ceramide;
a cholesterol and/or lanosterol ester; and
VLCFA.

In some embodiments of this aspect, the disclosed formulations for topical administration further comprise isostearyl isostearate.

In other embodiments of this aspect, the disclosed formulations for topical administration further comprise a therapeutically effective amount of phytosphingosine.

In other embodiments of this aspect, the disclosed formulations for topical administration further comprise an acidifying agent to maintain a pH in the range of 4.6 to 5.6, wherein the acidifying agent is gluconolactone, lactobionic acid, or an α-hydroxyacids, a β-hydroxyacids, or another polyhydroxy acid, or combinations thereof.

In other embodiments of this aspect, the disclosed formulations for topical administration further comprise a calcium chelator, wherein the calcium chelator is ethylenediaminetetraacetic acid (EDTA) or phytic acid.

In other embodiments of this aspect, the disclosed formulations for topical, intralesional, oral or parenteral administration further comprise a therapeutically effective amount of nicotinamide.

In other embodiments of this aspect, the disclosed formulations for topical, intralesional or parenteral administration further comprise a therapeutically effective amount of 18β-glycyrrhetinic acid, glycyrrhizic acid, carbenoxolone, chenodeoxycholic acid, or PF-877423, or combinations thereof.

In other embodiments of this aspect, the disclosed formulations for topical, intralesional, oral, or parenteral administration further comprise a therapeutically effective amount of hydrocortisone or an analog thereof, including, for example, the synthetic glucocorticoids kenelog/triamcinolone, clobetasol, betamethasone, fluticasone, fluocinonide, etc., or combinations thereof.

In some embodiments of this aspect, the ceramide included in the disclosed formulations is chosen from at least one of Cer 1 [EOS], Car 2 [NS], Cer 3 [NP], Car 4 [EOH], Cer 5 [AS], Cer 6 [AP], Cer 7 [AH], Cer 8 [NH], and Cer 9 [EOP].

In some embodiments of this aspect, the cholesterol and/or lanosterol ester included in the disclosed formulations is chosen from at least one of cholesterol oleate, cholesterol laurate, cholesterol myristate, cholesterol palmitate, cholesterol stearate, cholesterol arachidate, cholesterol behenate, cholesterol lignocerate, cholesterol cerotate, cholesterol montanate, cholesterol melissate, lanosterol oleate, lanosterol laurate, lanosterol myristate, lanosterol palmitate, lanosterol stearate, lanosterol arachidate, lanosterol behenate, lanosterol lignocerate, lanosterol cerotate, lanosterol montanate, and lanosterol melissate.

In some embodiments of this aspect, the VLCFA included in the disclosed formulations is chosen from at least one of lignoceric acid, cerotic acid, montanic acid, and melissic acid, and preferably chosen from at least one of cerotic acid, montanic acid, and melissic acid.

In this first aspect, the disclosed formulations for topical administration are compositions wherein the concentrations of the different ingredients in percent weight per weight (w/w), if present, range as follows:

ceramide, 0.0001-10% (w/w);
cholesterol and/or lanosterol ester, 0.0001-10% (w/w);
VLCFA, 0.01-10% (w/w);
phytosphingosine, 0.0001-10% (w/w);
isostearyl isostearate, 0.01-10% (w/w);
acidifying agent to maintain a pH of 5.0-5.6, X-Y % w/w);
EDTA or phytic acid, 0.01-2.0% (w/w);
nicotinamide, when present, 0.1-10.0% (w/w),
18β-glycyrrhetinic acid, glycyrrhizic acid, carbenoxolone, chenodeoxycholic acid, or PF-877423, or combinations thereof, when present, 0.0001-10% (w/w),
hydrocortisone, or an analog thereof, including, for example, the synthetic glucocorticoids kenelog/triamcinolone, clobetasol, betamethasone, fluticasone, fluocinonide, etc., or combinations thereof, when present, 0.05-10.0% (w/w), and
gluconolactone, when present, 0.1-8.0% (w/w).

In a second aspect, the disclosed formulations for topical administration are a composition comprising therapeutically effective amounts of at least one of each of the following:

18β-glycyrrhetinic acid, glycyrrhizic acid, carbenoxolone, chenodeoxycholic acid, or PF-877423, or combinations thereof; and
hydrocortisone, or an analog thereat including, for example, the synthetic glucocorticoids kenelog/triamcinolone, clobetasol, betamethasone, fluticasone, fluocinonide, etc., or combinations thereof.

In this second aspect, the disclosed formulations for topical administration are a composition wherein the concentrations of the different ingredients in percent weight per weight (w/w) range as follows:

18β-glycyrrhetinic acid, glycyrrhizic acid, carbenoxolone, chenodeoxycholic acid, or PF-877423, or combinations thereof, 0.0001-10% (w/w), and
hydrocortisone, or an analog thereof, including, for example, the synthetic glucocorticoids kenelog/triamcinolone, clobetasol, betamethasone, fluticasone, fluocinonide, etc., or combinations thereof, 0.001-10.0% (w/w).

In some embodiments of this aspect, the disclosed formulations for topical administration further comprise therapeutically effective amounts of at least one of each of the following:
a ceramide;
a cholesterol and/or lanosterol ester; and
a VLCFA.

In some embodiments of this aspect, the disclosed formulations for topical administration further comprise isostearyl isostearate.

In some embodiments of this aspect, the disclosed formulations for topical administration are compositions wherein the concentrations of the different ingredients in percent weight per weight (w/w), if present, range as follows:

ceramide, 0.0001-10% (w/w);
cholesterol ester, 0.0001-10% (w/w);
VLCFA, 0.001-10% (w/w); and
isostearyl isostearate, 0.01-10% (w/w).

In a third aspect the disclosed formulations for topical administration are formulations comprising any of the preceding components, and further comprising at least one dermatologically acceptable diluent or vehicle, thickener, humectant, emulsifier, emollient, structure agent, conditioning agent, antioxidant, preservative or pH adjuster.

In this aspect, the dermatologically acceptable diluents or vehicles comprise water, a dermatologically acceptable alcohol, or petrolatum, or combinations thereof.

Patient Population:

The disclosed formulations are intended for use on mammalian skin, including, for example, the skin of humans, domestic pets, livestock and other farm animals. When used on human subjects, or human patients in need of such treatment, the human patients may be of any age or gender, although specific formulations may be developed for treating human patients within specific age ranges, or of a particular gender.

Diseases, Disorders and Conditions to Treat:

The disclosed formulations are intended to treat diseases or disorders or conditions of the skin and mucous membranes which result in, or are characterized by, disruptions or dysfunctions of the epidermal barrier, and dermal or epidermal inflammation, or which are characterized by inflammation, irritation, abnormal desquamation and/or alterations in the epidermal microbiome. The disclosed formulations may also be used prophylactically, in order to prevent, or lessen the symptoms of a disease, disorder, or condition before it fully develops.

As such, the disclosed formulations may be used for treating, lessening the symptoms of, or preventing the symptoms of any of the following diseases, disorders, or conditions:

a) Atopic and seborrheic dermatitis and other genetically predisposed dermatitides;
b) Eczematous dermatitis induced by environmental or occupational insults, specifically allergic and irritant contact, eczema craquelee, radiation and stasis dermatitis;
c) Ulcers and erosions due to cutaneous trauma including chemical or thermal burns or vascular compromise or ischemia including venous, arterial, embolic or diabetic ulcers;
d) ichthyoses;
e) Epidermolysis bullosa;
f) Psoriasis and other papulosquamous disorders;
g) Cutaneous changes of intrinsic aging such as xerosis or Grover's Disease and/or dermatoheliosus;

h) Mechanical friction blistering;
i) Corticosteroid atrophy, for reversal and prevention;
j) Cutaneous lupus erythematosus including acute and chronic cutaneous lupus;
k) Steroid responsive dermatoses;
l) Rosacea;
m) Photodermatoses including idiopathic photodermatoses such as polymorphic or polymorphous light eruption (PMLE), chronic actinic dermatitis, solar urticaria, actinic prurigo, and hydroa vacciniforme; genetic photodermatoses including cutaneous porphyrias, Bloom's syndrome, xeroderma pigmentosum, reticular erythematous mucinosis, and subacute cutaneous lupus erythematosus; metabolic photodermatoses, including porphyrias and pellagra; and exogenous photodermatoses including drug-induced photosensitivity (both phototoxic and photoallergenic), pseudoponphyria, and phytophotodermatitis; as well as other underlying skin disorders that are exacerbated by exposure of the skin to sunlight, including Darier's disease, *Herpes simplex*, vitiligo, lupus, cutaneous lupus, and dermatomyositis;
n) Symptoms of mycosis fungoides, a cutaneous T-cell lymphoma also known as Alibert-Bazin syndrome or granuloma fungoides;
o) Acne;
p) Flushing of the skin; and
q) Keratosis Pilaris.

The disclosed formulations for topical administration may also be used to fortify the epidermal barrier of a patient in order to prevent or reduce symptoms of an occupationally or environmentally induced or genetically predisposed cutaneous disorder, by administering a therapeutically effective amount of a disclosed formulation to the skin of such a patient.

The disclosed formulations for topical administration may also be used to fortify the epidermal barrier of a premature infant under 33 weeks gestational age, by administering a therapeutically effective amount of a disclosed formulation to the skin of such a premature infant.

The disclosed formulations for topical administration may also be used to prevent or reduce cutaneous irritation or disruption of the epidermal barrier in patients being administered a therapeutic agent which produces cutaneous irritation and/or disrupts the epidermal barrier, by administering a therapeutically effective amount of a disclosed formulation to the skin of such a patient, prior to, concurrent with, or after administration of the therapeutic agent which produces cutaneous irritation and/or disrupts the epidermal barrier.

The disclosed formulations for topical administration may also be used to protect skin that is to be exposed to ionizing radiation, by administering a therapeutically effective amount of a disclosed formulation to the skin that is to be exposed to ionizing radiation, prior to that skin being exposed the ionizing radiation.

Methods of Treatment:

The methods of treatment to be employed with the disclosed formulations will vary depending upon the disease, disorder, or condition to be treated, and its severity. The methods will also vary depending upon the nature of the subject to be treated; their species, gender, and age, etc. Optimal methods of treatment, including the choice of specific formulation, the form of that formulation, the frequency of administration, and the duration of treatment will be adjusted according to the response of the patient, and the efficacy of the treatment, as will be judged by the patient themselves, or by a health care provider who is directing the treatment. Specific details regarding the methods of treatment can be defined by a health care provider overseeing the treatment, or by the patient, as results are obtained. Effective results will, in most cases, be achieved by topical application of a disclosed formulation in a thin layer directly over the affected area or areas, or in the area where one seeks to obtain a desired result.

In some embodiments, treatment may consist of topical application of thin layers of particular disclosed formulations in a particular order. In other embodiments, treatment may consist of topical application of thin layers of particular disclosed formulations in a particular order, interspersed with over-the-counter formulations, such as 1% hydrocortisone cream. For example, in some embodiments, treatment may consist of topical application of a thin layer of a cream formulation, such as Exemplary Formulation C or Exemplary Formulation D, followed by topical application of a thin layer of an ointment formulation, such as Exemplary Formulation A. In other embodiments, treatment may consist of topical application of a thin layer of a cream formulation, such as Exemplary Formulation C, followed by topical application of a thin layer of an over-the-counter formulation of 1% hydrocortisone cream, followed by topical application of a thin layer of an ointment formulation, such as Exemplary Formulation A. Alternatively, in other embodiments, treatment may consist of topical application of a thin layer of a cream formulation, such as Exemplary Formulation D which contains 1% hydrocortisone, followed directly by topical application of a thin layer of an ointment formulation, such as Exemplary Formulation A. In still other embodiments, treatment may consist of topical application of a thin layer of a lotion formulation, such as Exemplary Formulation B, followed by topical application of a thin layer of an ointment formulation, such as Exemplary Formulation A. In such multi-layer applications, the ointment formulation would usually be the last to be applied, so that it can form a more impervious external barrier and facilitate trans-epidermal diffusion of the contents of the underlying layers.

Depending upon the disease, disorder, or condition to be treated, and its severity, and whether the treatment is being done for therapeutic or prophylactic reasons, effective results may be obtained with application rates of from one application every week, to once every day, to multiple applications per day. In some embodiments the Exemplary Formulations are applied twice a day, with a first application at the start of a patient's day, following a bath or shower, and the second application at the end of the day, immediately prior to the patient retiring for sleep. Traditionally, such applications would occur in the morning and evening, but the time of application can be adjusted to the patient's daily schedule or routine. In all embodiments, the duration of the treatment regimen can be adjusted according to the patient's needs and according to the patient's disease or disorder's response to the treatment. Treatment can either be discontinued, or its frequency lessened, once symptoms diminish or disappear. Alternatively, it may be advantageous for treatments to continue for a fixed period beyond the diminution or disappearance of symptoms, and in other cases, it may be advantageous for treatment to continue indefinitely as a prophylactic treatment in patients who suffer from chronic disruption of the epidermal barrier.

In other embodiments, the administration of particular subset of components described above can be via an oral, parenteral, or intralesional route, while another subset of components can be via a topical route. In other words, the methods of treatment may combine the oral, parenteral, or intralesional administration of a subset of components with the topical administration of another subset of components. These so-called "combined approaches" to administration of the components described above will necessarily take into account the pharmacological characteristics of each individual component, including the human body's ability to absorb, distribute, metabolize and excrete ("ADME") the individual components when administered either orally, parenterally, or intralesionally. These "combined approaches" to administration of the components will also necessarily take into account the toxicity of each individual component when administered orally, parenterally, or intralesionally. In some instances, the route of administration of a particular ingredient, such as, for example, ceramides and gluconolactone, will be limited to topical administration. For other ingredients, such as, for example, niacinamide, the route of administration may be topical, intralesional, parenteral, or oral, or some combination thereof. For still other ingredients, such as, for example, 18β-glycyrrhetinic acid or glycyrrhizic acid, the route of administration may be topical, intralesional, parenteral, or oral, or a combination thereof. When ingredients are to be administered parenterally, they can be administered via any suitable parenteral route, including, for example, subcutaneously, intramuscularly, intravenously, or intraperitoneally, or some combination thereof. When ingredients are to be administered intralesionally, they can be administered via percutaneous injection within a skin lesion. The preferred parenteral route used in such "combined approaches" will be chosen based upon a variety of characteristics, including improved efficacy and/or reduced toxicity and/or adverse effects that might arise through topical administration alone.

Concentrations/Dosages:

The concentrations of the various ingredients of the disclosed formulations may vary widely, and will vary according to the route of administration. A typical range of concentration for each ingredient in topical formulations is from about 0.001% to about 10%. For all components having an effect on the epidermal barrier, regardless of the route of administration, the amount of an ingredient to be incorporated is to be a therapeutically-effective amount. The specific concentrations of ingredients will depend upon the disease, disorder or condition being treated, its severity, and the treatment regimen, including the route of administration, being used. When taken into consideration, these factors will guide the skilled artisan in determining what final concentrations to use for the various ingredients.

The following examples are being provided for the purpose of illustration only. They are not intended to be limiting in any manner, and are not provided to specifically define or limit the scope of the disclosed formulations.

EXAMPLES

Exemplary Formulations
Exemplary Formulation A:
Provided herewith is a first exemplary formulation that is an ointment according to the disclosed formulations provided herein.
Manufacturing Procedure;
1. Combine all Phase A ingredients and heat mixture to 85° C.; mixing with moderate agitation.
2. Mix until all waxes have melted and the mixture becomes homogenous.
3. Cool to 75° C.
4. With mixture held at 75° C. add each Phase B component, one at a time, and mix until all have been melted and a homogenous mixture has been formed.
5. Slowly cool to 35° C. and package.

Exemplary Formulation A- Skin Treatment Ointment

| Phase | Component (INCI Nomenclature) | % by Weight | Function |
|---|---|---|---|
| A | Microcrystalline Wax | 8.750 | Viscosity Increasing Agent |
| A | Euphorbia cerifera (Candelilla) Wax | 0.01-10.0 | Skin Conditioning Agent |
| A | Ceramide 3 | 0.0001-5.0 | Skin Conditioning Agent |
| A | Phytosphingosine | 0.0001-5.0 | Skin Conditioning Agent |
| B | Petrolatum | 3.0-99.0 | Skin Conditioning Agent |
| B | Coco-Caprylate | 15.00 | Emollient |
| B | Caprylic/Capric Triglyceride | 16.97 | Skin Conditioning Agent |
| B | Paraffin | 4.00 | Skin Conditioning Agent |
| B | Isostearyl Isostearate | 0.01-8.0 | Emollient |
| B | Glycyrrhetinic Acid | 0.0001-5.0 | Skin Conditioning Agent |
| B | $C_{10-30}$ Cholesterol/ Lanosterol Esters | 0.0001-5.0 | Skin Conditioning Agent |

Exemplary Formulation B:
Provided herewith is a second exemplary formulation that is a lotion according to the disclosed formulations provided herein.
Manufacturing Procedure:
1. Disperse the xanthan gum in water and start heating to 70-75° C.
2. Add remaining Phase A ingredients while heating, mix until the niacinamide dissolves.
3. Mix Phase B ingredients together and heat to 75-80° C.
4. Mix until uniform.
5. Slowly add Phase B to Phase A and mix until uniform.
6. Homogenize at 3,500 RPM for 5 minutes with a Silverson Mixer Homogenizer (Silverson Machines, Inc.; East Long Meadow, MA).
7. Cool with mixing to 40-45° C.
8. Add Phase C (1,2-henanediol caprylyl glycol) and mix until uniform.
9. Cool with mixing to room temperature.
10. While mixing, adjust pH to 4.6 to 5.6 with Phase D (a 20% solution of gluconolactone).
11. Aliquot into packaging.

Exemplary Formulation B - Skin Treatment Lotion

| PHASE | COMPONENT (INCI NOMENCLATURE) | % BY WEIGHT | FUNCTION |
|---|---|---|---|
| A | WATER (AQUA) | 71.33 | DILUENT |
| A | XANTHAN GUM | 0.60 | THICKENER |
| A | DISODIUM EDTA | 0.05 | CHELATING AGENT |
| A | PROPANEDIOL | 2.00 | HUMECTANT |
| A | GLYCERIN | 1.00 | HUMECTANT |
| A | NIACINAMIDE | 0.40 | ACTIVE |
| B | POLYGLYCERYL-10 PENTASTEARATE, BEHENYL ALCOHOL, SODIUM STEAROYL LACTYLATE | 3.00 | EMULSIFIER |
| B | CAPRYLIC/CAPRIC TRIGLYCERIDE | 7.50 | EMOLLIENT |
| B | GLYCERYL STEARATE | 1.50 | EMULSIFIER |
| B | NEOPENTYL GLYCOL DIHEPTANOATE | 7.50 | EMOLLIENT |
| B | EUPHORBIA CERIFERA (CANDELILLA) WAX | 1.00 | STRUCTURE AGENT |

-continued

Exemplary Formulation B - Skin Treatment Lotion

| PHASE | COMPONENT (INCI NOMENCLATURE) | % BY WEIGHT | FUNCTION |
|---|---|---|---|
| B | CETYL ALCOHOL | 1.50 | EMULSIFIER |
| B | $C_{10-30}$ CHOLESTEROL/ LANOSTEROL ESTERS | 1.00 | CONDITIONING AGENT |
| B | CERAMIDE 3 | 0.05 | ACTIVE |
| B | GLYCYRRHETINIC ACID | 0.50 | ACTIVE |
| B | PHYTOSPINGOSINE | 0.10 | ACTIVE |
| C | 1,2-HEXANEDIOL, CAPRYLYL GLYCOL | 0.75 | PRESERVATIVE |
| D | WATER, GLUCONOLACTONE 20% | 0.22 | pH ADJUSTOR |

Exemplary Formulation C:

Provided herewith is a third exemplary formulation that is an crème according to the disclosed formulations provided herein.

Manufacturing Procedure:
1. Disperse the xanthan gum in water and start heating to 70-75° C.
2. Add remaining Phase A ingredients while heating, mix until the niacinamide dissolves.
3. Mix Phase B ingredients together and heat to 75-80° C.
4. Mix until uniform.
5. Slowly add Phase B to Phase A and mix until uniform.
6. Homogenize at 3,500 RPM for 5 minutes with a Silverson Mixer Homogenizer (Silverson Machines, Inc.: East Long Meadow, MA).
7. Cool with mixing to 40-45° C.
8. Add Phase C (1,2-henanediol, caprylyl glycol) and mix until uniform.
9. Cool with mixing to room temperature.
10. While mixing, adjust pH to 4.6 to 5.6 with Phase D (a 20% solution of gluconolactone).
11. Aliquot into packaging.

Exemplary Formulation C- Skin Treatment Cream

| PHASE | COMPONENT (INCI NOMENCLATURE) | % BY WEIGHT | FUNCTION |
|---|---|---|---|
| A | WATER (AQUA) | 50.01 | DILUENT |
| A | XANTHAN GUM | 0.40 | THICKENER |
| A | DISODIUM EDTA | 0.05 | CHELATING AGENT |
| A | PROPANEDIOL | 2.00 | HUMECTANT |
| A | GLYCERIN | 2.00 | HUMECTANT |
| A | NIACINAMIDE | 0.40 | ACTIVE |
| B | POLYGLYCERYL-10 PENTASTEARATE, BEHENYL ALCOHOL, SODIUM STEAROYL LACTYLATE | 5.00 | EMULSIFIER |
| B | PETROLATUM | 12.00 | EMOLLIENT |
| B | CAPRYLIC/CAPRIC TRIGLYCERIDE | 10.50 | EMOLLIENT |
| B | ISOSTEARYL ISOSTEARATE | 2.00 | EMOLLIENT |
| B | GLYCERYL STEARATE | 1.50 | EMULSIFIER |
| B | NEOPENTYL GLYCOL DIHEPTANOATE | 9.00 | EMOLLIENT |
| B | EUPHORBIA CERIFERA (CANDELILLA) WAX | 1.00 | STRUCTURE AGENT |
| B | CETYL ALCOHOL | 1.50 | EMULSIFIER |
| B | $C_{10-30}$ CHOLESTEROL/ LANOSTEROL ESTERS | 1.00 | CONDITIONING AGENT |
| B | CERAMIDE 3 | 0.05 | ACTIVE |
| B | PHYTOSPINGOSINE | 0.10 | ACTIVE |
| B | GLYCYRRHETINIC ACID | 0.50 | ACTIVE |
| C | 1,2-HEXANEDIOL, CAPRYLYL GLYCOL | 0.75 | PRESERVATIVE |
| D | WATER GLUCONOLACTONE 20% | 0.24 | pH ADJUSTER |

Exemplary Formulation D:

Provided herewith is a fourth exemplary formulation that is an crème comprising 1% hydrocortisone as an anti-inflammatory according to the disclosed formulations provided herein.

Manufacturing Procedure:
1. Disperse the xanthan gum in water and start heating to 70-75° C.
2. Add remaining Phase A ingredients while heating, mix until the niacinamide dissolves.
3. Mix Phase B ingredients together and heat to 75-80° C.
4. Mix until uniform, making certain that the hydrocortisone acetate is dissolved.
5. Slowly add Phase B to Phase A and mix until uniform.
6. Homogenize at 3,500 RPM for 5 minutes with a Silverson Mixer Homogenizer (Silverson Machines, Inc.; East Long Meadow, MA).
7. Cool with mixing to 40-45° C.
8. Add Phase C (1,2-henanediol caprylyl glycol) and mix until uniform.
9. Cool with mixing to room temperature.
10. While mixing, adjust pH to 4.6 to 5.6 with Phase D (a 20% solution of gluconolactone).
11. Aliquot into packaging.

Exemplary Formulation D - Skin Treatment Cream with 1% Hydrocortisone Acetate

| PHASE | COMPONENT (INCI NOMENCLATURE) | % BY WEIGHT | FUNCTION |
|---|---|---|---|
| A | WATER (AQUA.) | 49.01 | DILUENT |
| A | XANTHAN GUM | 0.40 | THICKENER |
| A | DISODIUM EDTA | 0.05 | CHELATING AGENT |
| A | PROPANEDIOL | 2.00 | HUMECTANT |
| A | GLYCERIN | 2.00 | HUMECTANT |
| A | NIACINAMIDE | 0.40 | ACTIVE |
| B | POLYGLYCERYL-10 PENTASTEARATE, BEHENYL ALCOHOL, SODIUM STEAROYL LACTYLATE | 5.00 | EMULSIFIER |
| B | PETROLATUM | 12.00 | EMOLLIENT |
| B | CAPRYLIC/CAPRIC TRIGLYCERIDE | 10.50 | EMOLLIENT |
| B | ISOSTEARYL ISOSTEARATE | 2.00 | EMOLLIENT |
| B | GLYCERYL STEARATE | 1.50 | EMULSIFIER |
| B | NEOPENTYL GLYCOL DIHEPTANOATE | 9.00 | EMOLLIENT |
| B | HYDROCORTISONE ACETATE | 1.00 | ANTI-INFLAMMATORY |
| B | EUPHORBIA CERIFERA CANDELILLA WAX | 1.00 | STRUCTURE AGENT |

-continued

Exemplary Formulation D - Skin Treatment Cream
with 1% Hydrocortisone Acetate

| PHASE | COMPONENT (INCI NOMENCLATURE) | % BY WEIGHT | FUNCTION |
|---|---|---|---|
| B | CETYL ALCOHOL | 1.50 | EMULSIFIER |
| B | $C_{10-30}$ CHOLESTEROL/ LANOSTEROL ESTERS | 1.00 | CONDITIONING AGENT |
| B | CERAMIDE 3 | 0.05 | ACTIVE |
| B | PHYTOSPINGOSINE | 0.10 | ACTIVE |
| B | GLYCYRRHETINIC ACID | 0.50 | ACTIVE |
| C | 1,2-HEXANEDIOL, CAPRYLYL GLYCOL | 0.75 | PRESERVATIVE |
| D | WATER, GLUCONOLACTONE 20% | 0.24 | pH ADJUSTER |

Exemplary Methods of Treatment
Cutaneous Lupus Erythematosus:

A patient presented with a three year history of cutaneous lupus erythematosus. She had been suffering from systemic lupus erythematosus for some time before the rash that is characteristic of cutaneous lupus erythematosus appeared on her chest, arms, neck and face.

Prior to treatment with a treatment regime utilizing the formulations of the present disclosure, this patient had been treated with several different treatment regimens representing the standard of care for cutaneous lupus erythematosus patients. In particular, she had been using over-the-counter and prescription topical creams and ointments, including maximal strength hydrocortisone cream applied multiple times per day, with little or no effect. She had been prescribed, and had taken, prednisone orally for several months, with little or no effect. She had been administered cortisone shots, with little or no effect. She had been prescribed, and had taken, courses of orally-administered plaquenyi, courses of orally-administered aspirin, and courses, of orally-administered chloroquin, with little or no effect. All attempts to reduce the patient's suffering from cutaneous lupus erythematosus had brought little to no relief.

The patient was instructed to topically apply to the affected areas, the cream of Exemplary Formulation C, followed by an over-the-counter 1% hydrocortisone cream, followed the ointment of Exemplary Formulation A, in sequential thin coatings at night. She was also instructed to topically apply to the affected areas, the cream of Exemplary Formulation C, followed by an over-the-counter 1% hydrocortisone cream, in sequential thin coatings in the morning.

Figure 2:
FIG. 2 depicts the chest and neck area of the same patient following twice-daily administration of the disclosed formulations for approximately three weeks, as described in the Examples section below.

FIG. 1 depicts the chest and neck area of this patient prior to treatment with the formulations of the present disclosure. FIG. 2 depicts the chest and neck area of the same patient after approximately 3 weeks of the treatment regimen described above.

What is being claimed is:

1. A composition comprising therapeutically effective amounts of at least one of each of the following:
   18β-glycyrrhetinic acid;
   a glucocorticoid;
   a ceramide;
   polyhydroxy acid to maintain a pH of 4.6-5.6;
   a therapeutically effective amount of niacinamide; and
   a chelating agent.

2. The composition of claim 1, further comprising a phytosphingosine.

3. The composition of claim 1, further comprising isostearyl isostearate.

4. The composition of claim 1, wherein the glucocorticoid comprises hydrocortisone.

5. The composition of claim 1, wherein the chelating agent comprises a calcium chelator.

6. The composition of claim 5, wherein the calcium chelator comprises at least one of ethylenediaminetetraacetic acid (EDTA) and phytic acid.

7. The composition of claim 1, further comprising a therapeutically effective amount of fluocinonide.

8. The composition of claim 1, wherein the glucocorticoid comprises at least one of: triamcinolone, clobetasol, betamethasone, and fluticasone.

9. The composition of claim 1, wherein the ceramide is chosen from at least one of Cer 1 [EOS], Cer 2 [NS], Cer 3 [NP], Cer 4 [EOH], Cer 5 [AS], Cer 6 [AP], Cer 7 [AH], Cer 8 [NH], and Cer 9 [EOP].

10. The composition of claim 1, further comprising a cholesterol/lanosterol ester.

11. The composition of claim 10, wherein the cholesterol and/or lanosterol ester is chosen from at least one of cholesterol oleate, cholesterol laurate, cholesterol myristate, cholesterol palmitate, cholesterol stearate, cholesterol arachidate, cholesterol behenate, cholesterol lignocerate, cholesterol cerotate, cholesterol montanate, cholesterol melissate, lanosterol oleate, lanosterol laurate, lanosterol myristate, lanosterol palmitate, lanosterol stearate, lanosterol arachidate, lanosterol behenate, lanosterol lignocerate, lanosterol cerotate, lanosterol montanate, and lanosterol melissate.

12. The composition of claim 1, further comprising a very long chain fatty acid (VLCFA).

13. The composition of claim 12, wherein the VLCFA is chosen from at least one of lignoceric acid, cerotic acid, montanic acid, and melissic acid.

14. The composition of claim 1, further comprising a mixture of $C_{10}$-$C_{30}$ cholesterol/lanosterol esters.

15. The composition of claim 1, wherein the polyhydroxy acid is gluconolactone.

16. A composition comprising therapeutically effective amounts of the following concentrations of ingredients, in percent weight per weight (w/w):
   a ceramide, 0.0001-10% (w/w);
   at least one of 18β-glycyrrhetinic acid, glycyrrhizic acid, carbenoxolone, chenodeoxycholic acid, and PF-877423, 0.0001-5% (w/w);
   nicotinamide, 0.01-10.0% (w/w);
   at least one of hydrocortisone, triamcinolone, clobetasol, betamethasone, fluticasone, and fluocinonide, 0.001-10.0% (w/w); and
   polyhydroxy acid to maintain a pH of 4.6-5.6.

17. The composition of claim 16, further comprising therapeutically effective amounts of the following concentrations of ingredients, in percent weight per weight (w/w):
   a cholesterol and/or lanosterol ester, 0.0001-10% (w/w);
   ethylenediaminetetraacetic acid (EDTA) or phytic acid, 0.01-2.0% (w/w);
   nicotinamide, 0.01-10.0% (w/w); and
   gluconolactone, 0.01-8.0% (w/w).

18. The composition of claim 16, further comprising therapeutically effective amounts of the following concentrations of ingredients, in percent weight per weight (w/w):
   a very long chain fatty acid (VLCFA), 0.01-10% (w/w);
   phytosphingosine, 0.0001-10% (w/w); and
   isostearyl isostearate, 0.01-10% (w/w).

19. A composition comprising therapeutically effective amounts of at least one of each of the following:
   a ceramide;
   polyhydroxy acid in an amount to maintain a pH of 4.6-5.6;
   a therapeutically effective amount of nicotinamide;
   a chelating agent;
   18β-glycyrrhetinic acid;
   hydrocortisone; and
   gluconolactone.

20. The composition of claim 19, further comprising therapeutically effective amounts of:
   a cholesterol and/or lanosterol ester; and
   a very long chain fatty acid (VLCFA).

* * * * *